United States Patent
Bedair et al.

(10) Patent No.: US 8,501,117 B1
(45) Date of Patent: Aug. 6, 2013

(54) APPARATUSES, SYSTEMS, AND METHODS UTILIZING CAPILLARY ACTION

(75) Inventors: Sarah S. Bedair, Pittsburgh, PA (US); Gary K. Fedder, Turtle Creek, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 921 days.

(21) Appl. No.: 11/810,209

(22) Filed: Jun. 5, 2007

Related U.S. Application Data

(60) Provisional application No. 60/810,995, filed on Jun. 5, 2006.

(51) Int. Cl.
*B01L 3/00* (2006.01)
*G01N 7/00* (2006.01)
*G01N 1/10* (2006.01)

(52) U.S. Cl.
USPC ............. 422/507; 422/83; 422/500; 422/501; 422/502; 422/503; 422/504; 436/180

(58) Field of Classification Search
USPC ...................................... 422/83, 99; 436/180
See application file for complete search history.

(56) References Cited

U.S. PATENT DOCUMENTS

| | | | |
|---|---|---|---|
| 5,512,131 A | 4/1996 | Kumar et al. | |
| 6,458,426 B1 | 10/2002 | Bulovic et al. | |
| 6,495,944 B2 | 12/2002 | Hirano et al. | |
| 6,686,184 B1 | 2/2004 | Anderson et al. | |
| 2004/0038426 A1* | 2/2004 | Manalis | 436/514 |
| 2005/0064581 A1 | 3/2005 | Manalis et al. | |

OTHER PUBLICATIONS

Fedder et al. (Laminated High-Aspect-Ratio Microstructures in a Conventional CMOS Process, IEEE 1996, pp. 13-18).*
Keun-Ho Kim, Nicolaie Moldovan, Changhong Ke, and Horacio D. Espinosa, "A Novel AFM Chip for Fountain Pen Nanolithography—Design and Microfabrication"; Materials Research Society Symposium Proceedings; vol. 782, 2003 Fall MRS Meeting, A5.56.1, 2004.
P.F. Man, C.H. Mastrangelo, M.A. Burns, D.T. Burke, Microfabricated Capillary-Driven Stop Valve and Sample Injector, 1998 IEEE 11th Annual International Workshop on Micro Electro Mechanical Systems, 45-50, Heidleburg, Germany, Jan. 25-29, 1998.
Patel, R., Rongnong, Z., Zinszer, K., Josse, F., Cernosek, R., Real-Time Detection of Organic Compounds in Liquid Environments Using Polymer-Coated Thickness Shear Mode Quartz Resonators, Analytical Chemistry, Oct. 15, 2000, pp. 488-4898, vol. 72, No. 20, Amer. Chem. Society.
Ricco, A. J., Kepley, L.J., Thomas, R.C., Sun, L., Crooks, R.M., Self-Assembling Monolayers on Saw Devices for Selective Chemical Detection, 1992 IEEE, pp. 114-117, Sandia National Laboratories and University of New Mexico.
Hierlemann, A., Baltes, H.,CMOS-based chemical microsensors, The Analyst, 2003, pp. 15-28, vol. 128, Royal Society of Chemistry.

(Continued)

*Primary Examiner* — Dean Kwak
(74) *Attorney, Agent, or Firm* — Downs Rachlin Martin PLLC

(57) ABSTRACT

Apparatuses, systems, and methods utilizing capillary action and to control the movement or placement of liquids or other materials in micro-devices and nano-devices. In some embodiments, the present invention may be used to control polymer addition to micro-cantilevers and nano-cantilevers for biological sensing, chemical sensing, and other sensing. In other embodiments, the present invention may be used to deliver adhesives, dielectrics, chemo resistor materials, and other materials to micro-devices and nano-devices.

15 Claims, 25 Drawing Sheets

OTHER PUBLICATIONS

Lange, D., Hagleitner, C., Hierlemann, A., Brand, O., Baltes, H., Complementary Metal Oxide Semiconductor Cantilever Arrays on a Single Chip: Mass-Sensitive Detection of Volatile Organic Compounds, Analytical Chemistry, Jul. 1, 2002, pp. 3084-3095, vol. 74, No. 13, Amer. Chem. Society.

Fritz, J., et al., Translating Biomolecular Recognition into Nanomechanics, Science, 2000, pp. 316-318, vol. 288, AAAS.

Fritz, J., Baller, M.K., Lang, H.P., Rothuizen, H., Vettiger, P., Meyer, E., Guntherodt, H.J., Gerber, CH., Gimzewski, J.K., Translating Biomolecular Recognition into Nanomechanics, Science, Apr. 14, 2000, pp. 316-318, vol. 288.

Baltes, H., Lange, D., Koll, A., The electronic nose in Lilliput, IEEE Spectrum, Sep. 1998, pp. 35-38.

Bietsch, A., Zhang, J., Hegner, M., Lang, H.P., Gerber, C., Rapid functionalization of cantilever array sensors by inkjet printing, Nanotechnology, 2004, pp. 873-880, vol. 15, Institute of Physics Publishing.

Fedder, G.K., Santhanam, S., Reed, M.L., Eagle, S.C., Guillou, D.F., Lu, M.S.C., Carley, L.R., Laminated High-Aspect-Ratio Microstructures in a Convential CMOS Process, IEEE, 1996, pp. 13-18.

Bedair, S.S., Fedder, G.K., CMOS MEMS Oscillator for Gas Chemical Detection, IEEE, 2004, pp. 995-958.

Aoyama, R., Seki, M., Hong, J.W., Fujii, T., Endo, I., Novel Liquid Injection Method with Wedge-Shaped Microchannel on a PDMS Microchip System for Diagnostic Analyses, Tranducers '01 Eurosensors XV, 11th Interl. Conference on Solid State Sensors and Actuators, Munich GE, Jun. 10-14, 2001, pp. 1-6.

Delamarche, E., Bernard, A. Schmid, H., Bietsch, A., Michel, B., Biebuyck, H., Microfluidic Networks for Chemical Patterning and Substrates: Design and Application to Bioassays, J. Amer. Chem. Soc. 1998, pp. 500-508, vol. 120, vol. 120, American Chemical Society.

Delamarche, E., Bernard, A., Schmid, H., Michel, B., Biebuyck, H., Patterned Delivery of Immunoglobulins to Surfaces Using Microfluidic Networks, Science, May 2, 1997, pp. 779-781, vol. 276.

Kim, E., Xia, Y., Whitesides, G.M., Micromolding in Capillaries: Applications in Materials Science, J. Amer. Chem. Soc. Jan. 17, 1996, pp. 5722-5731, vol. 118, America Chemical Society.

Xia, Y., Whitesides, G.M., Soft Lithography, Agnew. Chem. Int., 1998, pp. 550-575, Ed. 37.

Jackman, R.J., Duffy, D.C., Ostuni, E., Willmore, N.D., Whitesides, G.M., Fabricating Large Arrays of Microwells with Arbitrary Dimensions and Filling them Using Discontinuous Dewetting, Anal. Chem. Jun. 1, 1998, pp. 2280-2287, vol. 70, No. 11, American Chemical Society.

Chabinyc, M.L., Wong, W.S., Paul, K.E., Street, R.A., Fabrication of Arrays of Organic Polymeric Thin-Film Transistors Using Self-Aligned Microfluidic Channels, Adv. Mater, Nov. 17, 2003, pp. 1903-1907, vol. 15, No. 22.

Schierbaum, K.D., Gerlach, A., Haug, M., Gopel, W., Selective detection of organic molecules with polymers and supramolecular compounds: application of capacitance, quartz microbalance and calorimetric transducers, Sensors and Actuators A, 31 (1992) 130-137.

Burg, Thomas P., Mirza, Amir R., Milovic, Nebojsa, Tsau, Christine H., Popescu, George A., Foster, John S., Manalis, Scott R., Vacuum-Packaged Suspended Microchannel Resonant Mass Sensor for Biomolecular Detection, Journal of Microelectromechanical Systems, Dec. 2006, pp. 1466-1476, vol., 15, No. 6, IEEE.

* cited by examiner

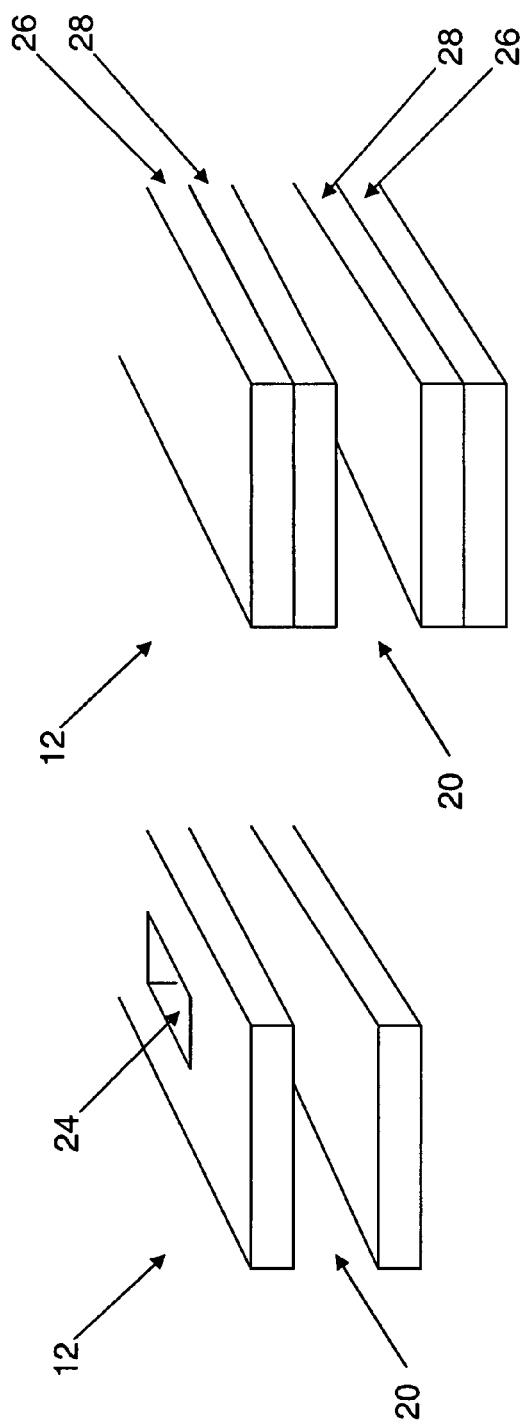

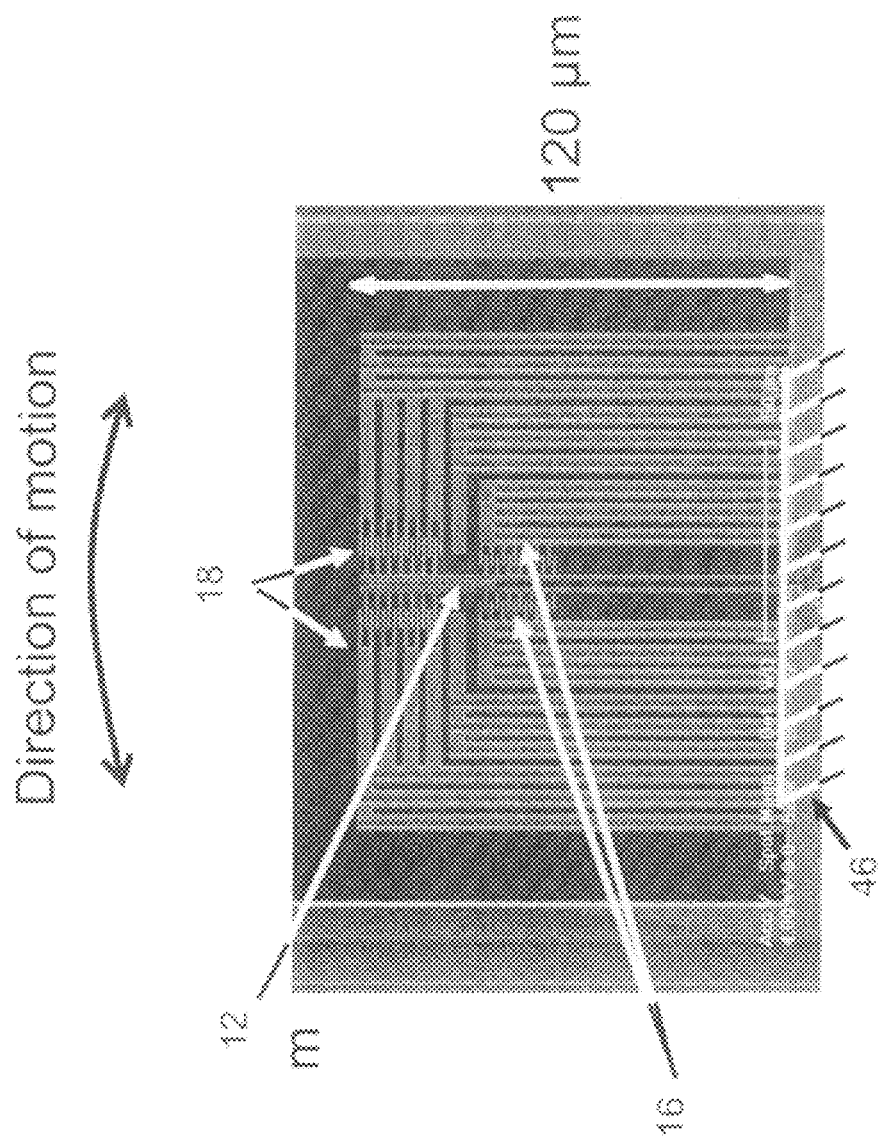

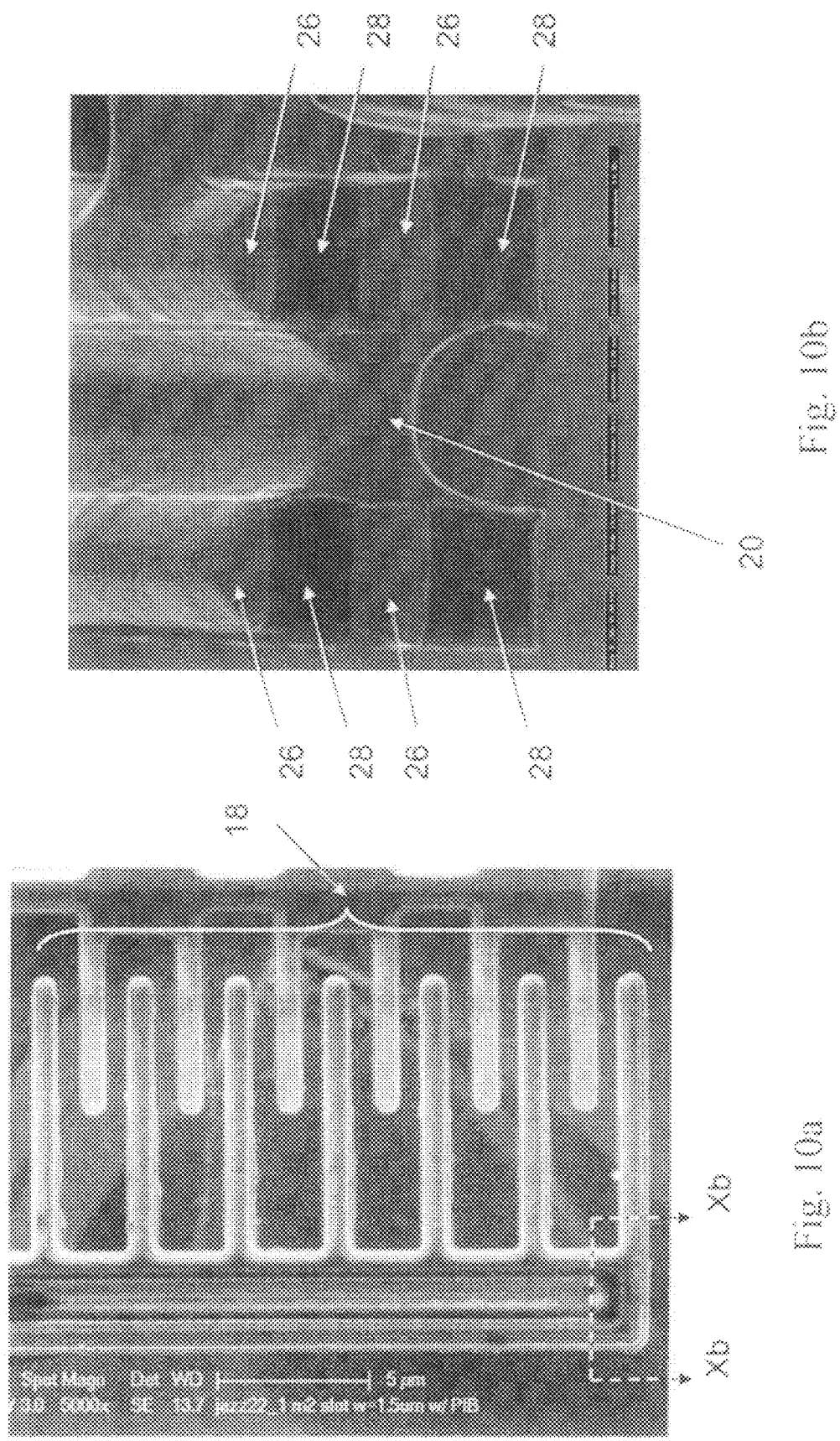

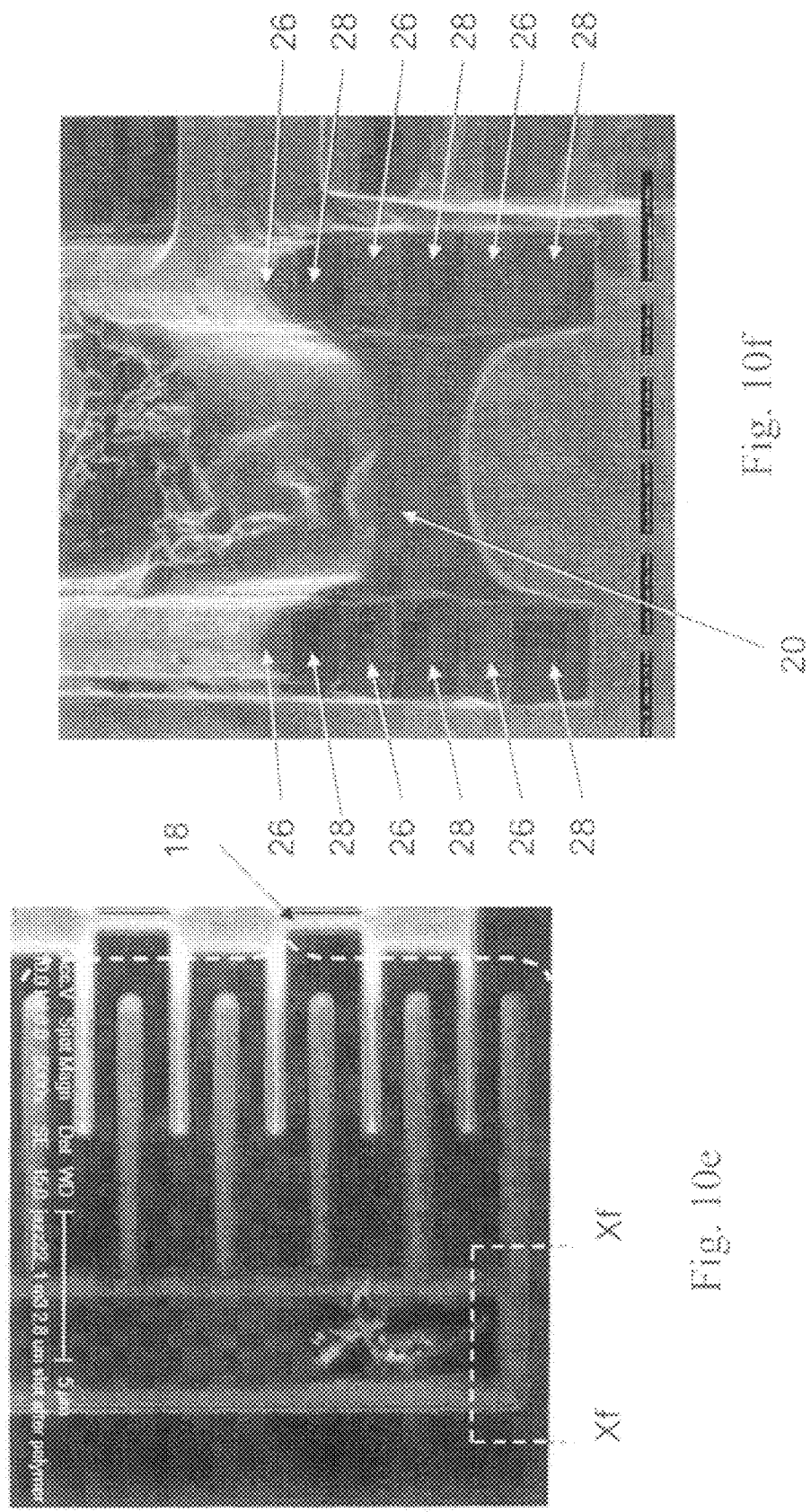

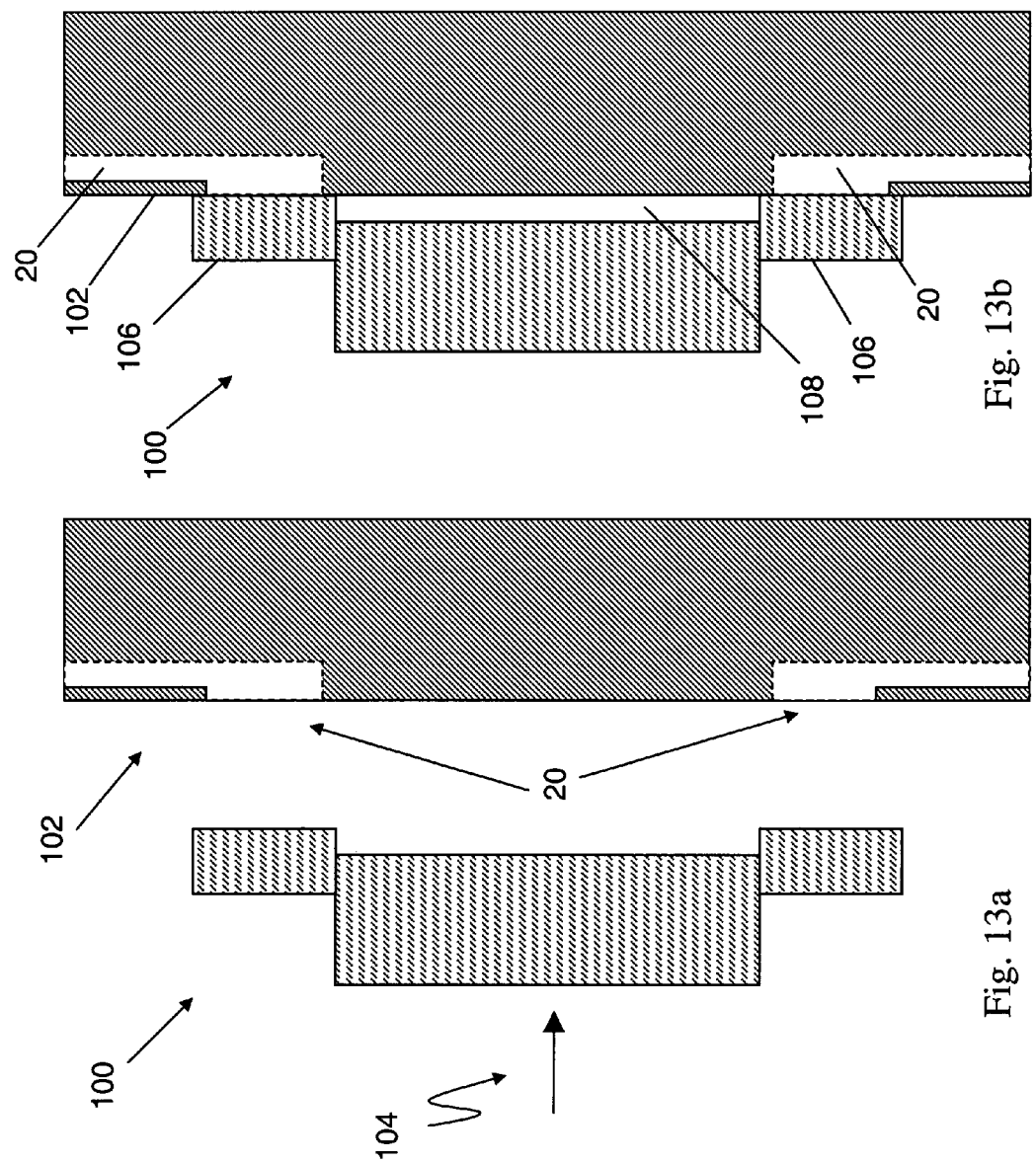

APPARATUSES, SYSTEMS, AND METHODS UTILIZING CAPILLARY ACTION

CROSS-REFERENCE TO RELATED APPLICATIONS

This application claims priority from U.S. Provisional Patent Application No. 60/810,995, filed Jun. 5, 2006, which is incorporated herein by reference.

STATEMENT REGARDING FEDERALLY-SPONSORED RESEARCH AND DEVELOPMENT

This invention was made, in part, with government support under Grant Number F49620-02-0359 awarded by AFOSR MURI and Grant Number 200-2002-00528 awarded by NIOSH/CDCP. The United States government may have certain rights in this invention.

FIELD OF THE INVENTION

The present invention is directed generally to apparatuses, systems, and methods utilizing capillary action and, more specifically, to methods and apparatuses to control the movement or placement of liquids or other materials in micro-devices and nano-devices.

BACKGROUND OF THE INVENTION

Single-chip electronic noses, enabled by full on-chip integration of gas chemical microsensors with signal-conditioning electronics have tremendous medical, environmental and safety applications. Gravimetric detection is an important sensing modality for these microsystems.

Commercially available mass-sensitive devices for volatile organic compound detection use piezoelectric quartz substrates. Thickness shear mode resonators (TSMR), also known as quartz micro-balances (QMB) (Patel, R., Zhou, R. Zinszer, K., and F. Josse, "Real-time detection of organic compounds in liquid environments using polymer-coated thickness shear mode quartz resonators", Analytical Chemistry, vol. 72, no. 20, p. 4888-4898, 2000) (Schierbaum, K. D., Gerlach, A., Haug, M., and W. Gopel, "Selective detection of organic molecules with polymers and supramolecular compounds: application of capacitance, quartz microbalance, and calorimetric transducers", Sensors and Actuators A, 31, p. 130-137, 1992), and Rayleigh surface acoustic wave (SAW) devices (Ricco, A. J., Kepley, L. J., Thomas, R. C., Sun, L., and R. M. Crooks, "Self-assembling monolayers on SAW devices for selective chemical detection", IEEE Solid-State Sensor & Actuator Workshop, Hilton Head, S.C. June 22-25, p. 114-117, 1992) are examples of such devices. However, these piezoelectric devices have not been fully integrated with on chip electronics. In contrast, resonant cantilever chemical microsensors integrated with CMOS have been demonstrated (A. Hierlemann and H. Baltes, "CMOS-based chemical microsensors", Analyst, 128, p. 15-28, 2003). Prior work on cantilever mass sensors includes detection of humidity, mercury vapor, and volatile organic compounds (Lange, D., Hagleitner, C., Hierlemann, A., Brand, O., and H. Baltes, "Complementary Metal Oxide Semiconductor Cantilever Arrays on a Single Chip: Mass-Sensitive Detection of Volatile Organic Compounds", Analytical Chemistry, vol. 74., no. 13, p. 3084-3095, 2002) as well as biomolecular recognition in a liquid media (Fritz, J., Bailer, M. K., Lang, H. P., Rothuizen, H., Vettiger, P., Meyer, E., Guntherodt, H. J., Gerber, Ch., and J. K. Gimzewski, "Translating biomolecular recognition into nanomechanics", Science, 288, p. 316-318, 2000.). Post-CMOS micromachining has been used to make fully integrated mass sensitive oscillators with pico-gram resolution (H. Baltes, D. Lange, A. Koll, "The electronic nose in Lilliput," IEEE Spectrum, 9, 35, (1998)). These devices were formed through deposition of precise amounts of a chemically sensitive layer onto relatively wide cantilevers.

Another example of a CMOS-MEMS resonant gas sensor used electrostatic actuation and detection to form a free-running oscillator (S. S. Bedair and G. K. Fedder, "CMOS MEMS Oscillator for Gas Chemical Detection," Proceedings of IEEE Sensors, Vienna, Austria, Oct. 24-27, 2004). A cantilever beam suspended a plate made large enough to accommodate drops of chemically sensitive polymer placed directly onto the plate using drop-on-demand ink jet deposition. Ink jet deposition can functionalize each cantilever in an arrayed structure with a separate polymer. This non-contact technology is scalable for large arrays, easy to use, versatile, and faster than other means of coating such as from micro-capillaries and drop casting from pipettes (A. Bietsch, J. Zhang, M. Hegner, H. P. Lang, and C. Gerber, "Rapid functionalization of cantilever array sensors by inkjet printing", 2004 Nanotechnology 15 873-880). Other thin film application methods include dip pen and shadow mask processing which are both time consuming processes.

Another prior microfluidic system is described in U.S. patent application, 20050064581 and in a corresponding paper (T. P. Burg, A. R. Mirza, N. Milovic, C. H. Tsau, G. A. Popescu, J. S. Foster and S. R. Manalis, "Vacuum-packaged suspended microchannel resonant maass sensor for biomolecular detection," J. Microelectromechanical Systems, December 2006). These prior art documents describe an enclosed microchannel. Material is flowed into the channel to functionalize sidewalls of the channel to capture biomolecules on the sidewalls. However, the channel in these works is not used or taught as a wicking structure for deposition of a non-liquid material, such as polymers, that fills or partly fills the channel. Specifically, the patent application describes a microfluidic channel to detect analyte that may have a liquid or gel in the channel. The analyte is flowed into the microchannel. The gel may be delivered by pressure flow or electrophoresis, but no description or teaching of gel deposition through wicking is provided. The invention requires an enclosed microchannel for analyte delivery through flow, and in order to package in vacuum.

It is beneficial to further scale down the size of the resonant microstructure to achieve an increased mass sensitivity and reduced cost. Scaling cantilevers down to micro- and nano-scale dimensions is achievable with optical or piezoresistive resonant detection. However, microstructures with low-noise electrostatic actuation and detection require narrow air gaps that are generally incompatible with existing polymer deposition techniques.

Accordingly, there is a need for improved apparatuses and methods to control polymer addition to micro-cantilevers and nano-cantilevers for biological and chemical sensing. Those and other advantages of the present invention will be described in more detail hereinbelow.

BRIEF SUMMARY OF THE INVENTION

The present invention is directed generally to apparatuses, systems, and methods utilizing capillary action. The present invention has many applications and many variations. For example, the present invention may be used in the operation of sensors. The present invention may be used to fill a space between two or more parts. In some embodiments, the present invention may be used to carry an adhesive to a desired location to fix two or more parts together. In other embodiments the present invention may be used to provide a dielectric between two or more electrodes or contacts. In another embodiment, the present invention may be used in a chemo resistor device in which electrically resistive material is positioned between two or more electrodes or contacts. The present invention may also be used with a mass sensor for gas chemical sensing applications. The present invention may also be used with many different fluids and materials, and in many specific applications such as to control material addition to micro-cantilevers and nano-cantilevers for biological sensing, chemical sensing, and other sensing.

In one specific embodiment, the present invention will be described in terms of apparatuses and methods to mass load a microstructure with polymer without affecting nearby gaps. Precise amounts of polymer or other materials, which may be suspended in solution, are wicked onto the microstructure through capillary action of micro-grooves formed along the length of the beam. The polymer or other material is left on the microstructure after drying of the solvent. Scaling down the mass of the mass sensitive cantilever leads to a higher mass sensitivity which leads to highly sensitive gas chemical sensing applications. The technique enables design of low-mass polymer-loaded cantilevers with electrostatic actuation and capacitive sensing for integrated gas chemical detector arrays.

The present invention may also include two or more devices formed in a single apparatus or on a single substrate. The single apparatus or substrate may contain several devices of the same type, such as to perform same test or operation many times. Alternatively, the single apparatus or substrate may contain several devices of different types, such as to perform a variety of different tests. In some embodiments, the devices receive different materials in their respective target areas, and in some embodiments they receive the same materials. As a result, redundant or different testing, sensing, or other functions may be performed on a single structure.

Although the present invention will generally be described in terms of specific embodiments, many variations, modifications, and other applications are possible with the present invention. These and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein:

FIGS. 2a-2h illustrate embodiments of wicking devices according to the present invention.

FIGS. 3b and 3c illustrate cross-sectional views along lines IIIb-IIIb and IIIc-IIIc, respectively, in FIG. 3a.

FIGS. 4a and 4b illustrate an embodiment of an electrostatically actuated resonator with differential comb drive and sensing electrodes.

FIGS. 10a-10g are scanning electron micrographs of several embodiments of the present invention.

FIGS. 13a and 13b illustrate another embodiment of the present invention in which one or more channels are used to provide an adhesive to secure two objects together.

DETAILED DESCRIPTION OF THE INVENTION

The present invention will be generally described in terms of specific examples and embodiments, although many variations and modifications are possible. For example, although the present invention is sometimes described in connection with the use of polystyrene, many other materials may be used with the present invention. For example, the present invention may be used with materials that can be delivered with solvents, and other materials in solution and fluids. For example, these materials can be active polymers, nano particles, polymer composites, biomolecules, solgel, electro- and magneto-active polymers, adhesives, and sealants. Furthermore, the present invention may be constructed in scales other than those specifically defined herein. For example, specific dimensions are provided in some examples, although smaller devices may be desirable to provide additional sensitivity in some applications, and larger devices may be desirable in other applications. Similarly, the use of the term "micro", such as in "micro-cantilever", "microstructure", "micro-capillary", and others, is illustrative and is not a limitation of the present invention. For example, the present invention may also be used at nano-scales or at smaller or larger scales.

Figure 1:
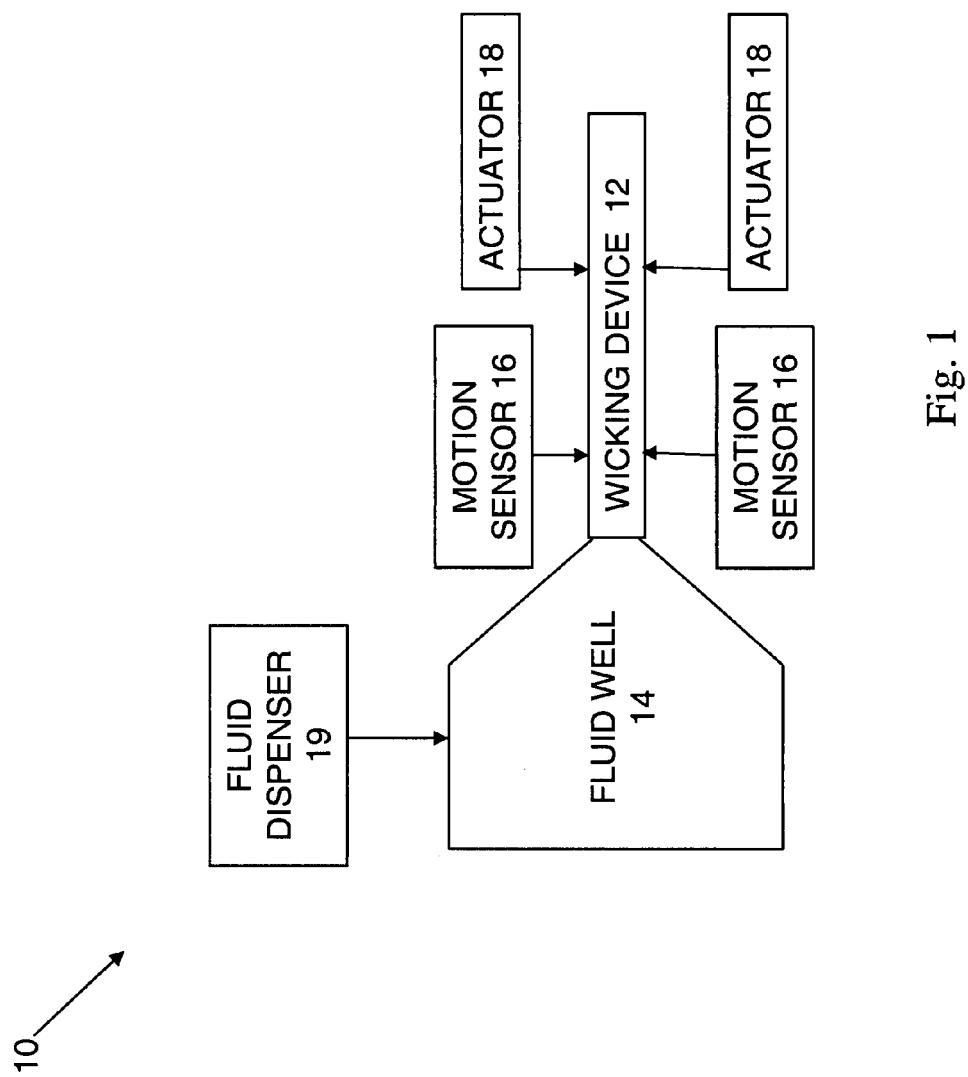
FIG. 1 illustrates one embodiment of an apparatus according to the present invention.

FIG. 1 illustrates one embodiment of an apparatus according to the present invention. In this embodiment the apparatus 10 is a sensor, although the apparatus of the present invention may take other forms, such as in assembling parts for microelectromechanical systems, providing adhesive, sealant, or other material between two or more parts, and in other applications.

In FIG. 1 the sensor 10 includes wicking device 12, a fluid well 14, motion sensors 16, actuators 18, and a fluid dispenser 19.

The wicking device 12 carries a fluid along a channel (not shown) in the wicking device 12 via capillary action. The wicking device 12 may be an elongated structure, such as a straight beam, or it may be a curved structure, or it may have other shapes. In some embodiments the wicking device is cantilevered, although it is not required to be cantilevered. The channel will be described in more detail hereinbelow and may take different forms, such as a gap between two surfaces, a groove or recess formed in a surface, or a passage through an object. In some embodiments, the material is deposited in the fluid well 14 and is wicked into the wicking device 12, so that the deposited material does not interfere or contact any other parts of the devices, such as the motion sensors 16 or the actuators 18.

In some embodiments the wicking device 12 will be suspended. As used herein, a "suspended" wicking device 12 means a significant portion of the wicking device 12 is surrounded by air, or void, or ambient conditions other than structural elements used to support the wicking device 12. For example, in some embodiments the wicking device 12 is in the form of a cantilevered beam supported at one end and suspended in air (or in other conditions) for most of its length. In other embodiments, the wicking device 12 is in the form of an object or layer formed over a recess, in which at least a portion of the object or layer is suspended over the recess. In some embodiments, the wicking device 12 can be formed from two or more parts or pieces, and in some cases all parts or pieces are suspended, and in other cases some parts or pieces are suspended and other parts or pieces are not suspended. Although several embodiments of the present invention will be described in terms of a suspended wicking device, advantages of the present invention may also be realized with wicking devices 12 that are not suspended in any way.

The fluid well 14 is the source of the fluid that is carried along the channel in the wicking device 12 via capillary action. The fluid well 14 is significantly larger than the channel in the wicking device 12 and directly receives the fluid, such as through an ink jet deposition or through other means such as micro capillaries and pipettes, dip pen, and shadow mask processing. The fluid well 14 will sometimes be referred to as a "target area", "target well area", and other names. These terms are interchangeable.

The motion sensors 16 detect motion of the wicking device 12. The motion sensors 16 are not required in the present invention, and some embodiments illustrated herein do not use the motion sensors 16.

The actuators 18 cause the wicking device 12 to move. The actuators 18 may, for example, cause motion through the application of electrostatic forces, or through other means. The actuators 18 are not required in the present invention, and some embodiments illustrated herein do not use the actuators 18.

The fluid dispenser 19 is oriented to dispense fluid into the fluid well. The fluid dispenser 19 may be, for example, drop-on-demand ink jet device, or a micro-pipette device, or a dip pen device, or it may be other forms of fluid dispensers 19. Unlike the prior art, the present invention dispenses or deposits the fluid into a fluid well 14, from which it is wicked onto the channel 20 or channels of the wicking device 12. Many variations are possible with the fluid dispenser 19. For example; there may be a dedicated fluid dispenser 19 for each fluid well, or one fluid dispenser 19 may be used with more than one fluid well 14, such as by moving the fluid well 14, moving the fluid dispenser 19, or otherwise changing the orientation of the fluid well 14 and the fluid dispenser 19. In some embodiments of the present invention, the fluid dispenser 19 is integrated into the device including the fluid well 14, and in other embodiments the fluid dispenser 19 is separate from the rest of the device and is engaged with the apparatus 10 when it is needed.

The sensor 10 illustrated in FIG. 1 is a gravimetric sensor in which the actuators 18 cause the wicking device to move, and the motion sensors 16 measure the movement. The frequency response of the wicking device is indicative of the mass, and the distribution of mass, of the wicking device 12 and any material deposited or absorbed on the wicking device 12. The frequency response of an empty wicking device 12 can be established, so that any change in the response is indicate of the additional material added to the wicking device 12. In this way, the mass of material deposited on the wicking device can be determined. A mass sensitive material can be deposited onto the wicking device. In this way, the mass of an additional material absorbed into the mass sensitive material on the wicking device can be determined. For example, the additional material to be determined can be a gas chemical analyte absorbed into a mass sensitive polymer. The present invention is not limited to use in gravimetric sensors, and may be used in other types of sensors 10, such as chemo-resist sensors, capacitive sensors, or other types of sensors. The present invention can also be used in apparatuses other than sensors, as will be described in more detail hereinbelow.

Many variations are possible with the present invention. For example, the sensor 10 may or may not include motion sensors 16 and actuators 18, or may contain a more or fewer motion sensors 16 and actuators 18 than shown herein. For example, a sensor 10 may include only one motion sensor 16 or actuator 18, or it may include more than two motion sensors 16 and actuators 18. Similarly, more than one fluid well 14 may be used, and more than one wicking device 12 may be used in the sensor 10. More than one wicking device 12 may be used for each fluid well 14. The sensor 10 may also include devices not shown in this figure, such as devices for applying and measuring electrical current and voltage, and other devices. In some embodiments, the sensor 10 includes sources of controlled electrical voltage or current, and devices for measuring one or more electrical characteristics, such as voltage, resistance, current, capacitance, and electromagnetic fields. These embodiments may also include motion sensors 16 and actuators 18, or the embodiments may exclude one or both of motion sensors 16 and actuators 18.

Figure 2A:
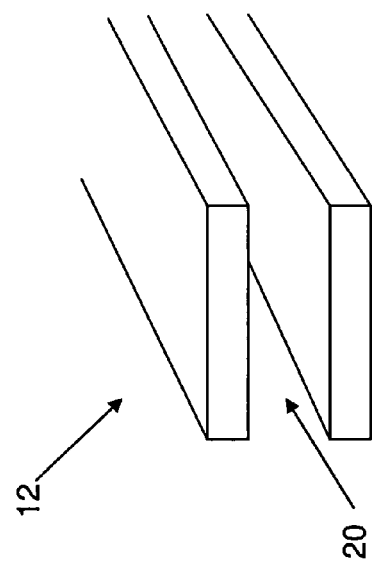

FIG. 2a illustrates one embodiment of a wicking device 12 according to the present invention. The wicking device 12 includes a channel 20 formed in the wicking device 12. The channel is in the form of a groove 20 and is defined by three surfaces of the wicking device 12.

Figure 2B:
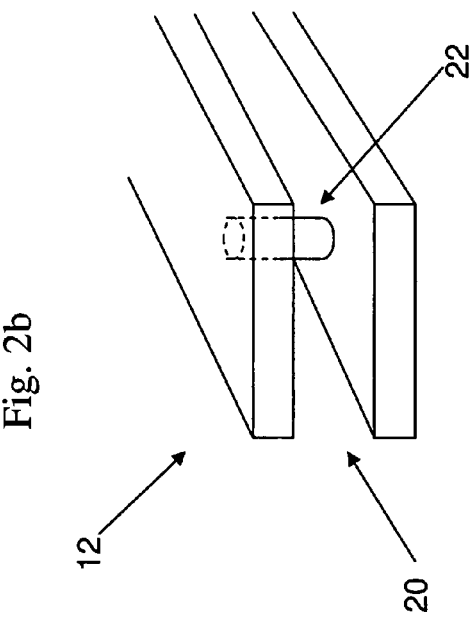

FIG. 2b illustrates another embodiment of the wicking device 12 in which the wicking device 12 is formed from two parallel plates and the channel 20 is defined by the space between the two plates. Although the plates are illustrated as being parallel, they may also be non-parallel.

Figure 2C:
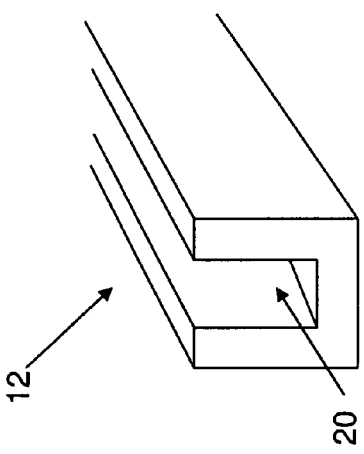

FIG. 2c illustrates another embodiment of the wicking device 12 in which two plates are oriented vertically and the channel 20 is formed between the vertical plates. In other embodiments the plates may have other orientations, such as 45 degrees and others.

Figure 2D:
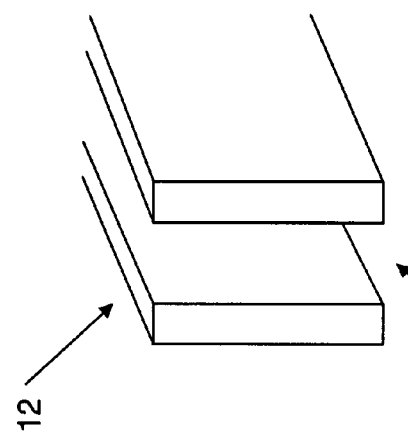

FIG. 2d illustrates another embodiment of the wicking device 12 in which one or more supports 22 are provided between the plates of the wicking device 12. The supports 22 resist the forces applied to the plates from the capillary action of fluids between the plates. As a result, the supports prevent the plates of the wicking device 12 from bending inward and touching each other.

Supports may also be included in other orientations of channels, such as in FIG. 2c. Supports 22 are shown in FIG. 2d as cylindrical and in the center of the channel, but supports can also be rectangular or other shapes and can be located at other locations in the channel.

FIG. 2e illustrates another embodiment of the wicking device in which at least one plate includes an opening 24. One or more plates or other parts of the wicking device 12 may include one or more openings. The openings may be of any shape, spacing, and orientation. The opening 24 reduces the mass of the wicking device and, in some applications, allows for increased sensitivity.

FIG. 2f illustrates another embodiment of the wicking device 12 in which more than two plates are used. In that embodiment, two of the plates 26 are electrical conductors, and the other two plates 28 are electrical insulators. This embodiment may be used, for example, when the sensor is measuring capacitance with the fluid in the channel 20 of the wicking device 12.

FIG. 2g illustrates another embodiment of the wicking device 12 in which the structure of the electrical conductor 26 and insulator 28 vary from the previous embodiment. In this embodiment, one of the electrical conductors 26 is embedded with one of the electrical insulators 28. These and other variations are possible.

Figure 2H:
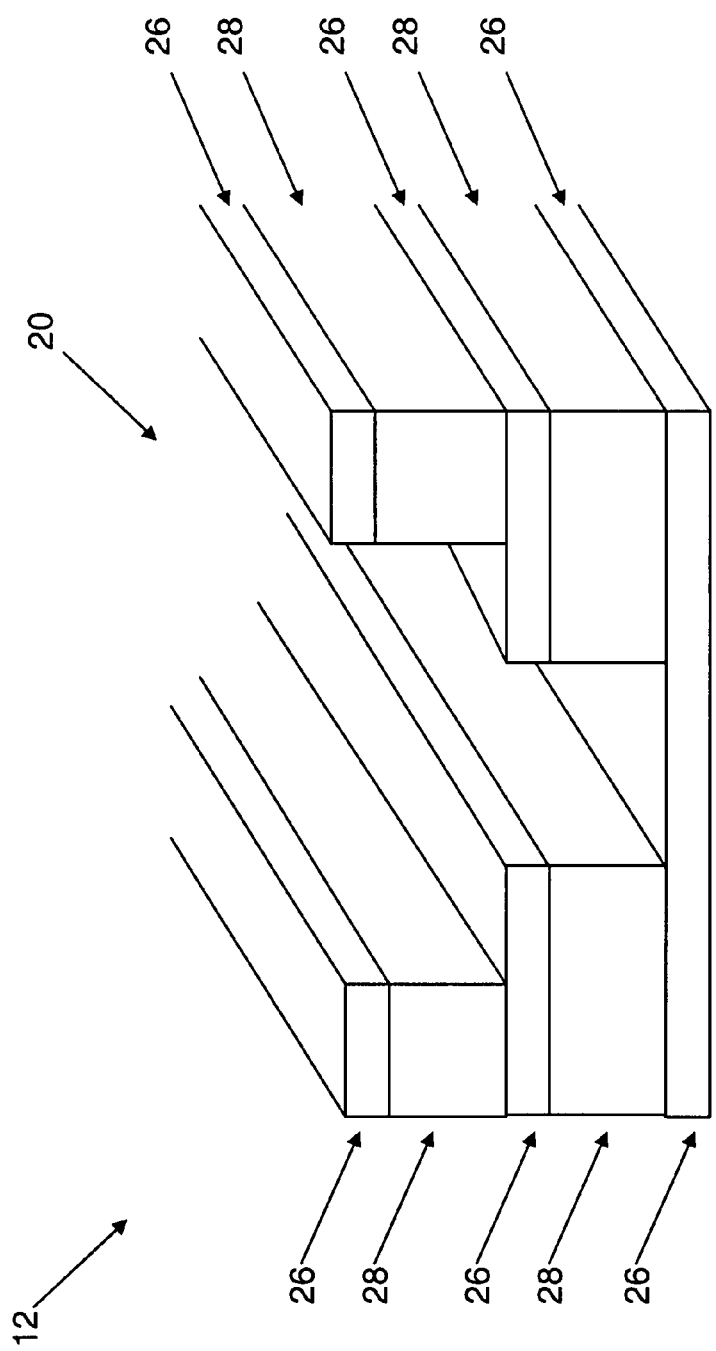

FIG. 2h illustrates another embodiment of the wicking device. In this embodiment, the channel 20 is formed in a more complex cross-sectional shape than in the previous embodiments. Also, there are several electrical conductors 26 and electrical insulators 28 on the walls of the channel 12. This embodiment may be used, for example, to measure electrical resistance of the material in the channel 20. Many combinations of measurements may be taken from the various electrical conductors 26. In other embodiments, for example, different numbers of electrical conductors 26, in different orientations, may be used. The electrical conductors 26 may be exposed to the channel 20 along the entire length of the channel, or the electrical conductors 26 may be exposed only in selected portions of the channel 20, such as at the end or at other locations.

Many other variations of the wicking device 12 are also possible. For example, although the wicking devices 12 are shown as being open at their ends, they may also be capped or closed at the ends, and the wicking devices 12 may include different numbers, orientations, and structures of plates and other components forming the wicking device 12 and defining the channel 20. In some embodiments, the channel 20 is tapered at the free end so as to wick more liquid to that end and, thereby, deposit addition material there. This results in non-uniform distribution of material, with more material at the free end where the device is more sensitive to mass. This embodiment, for example, may allow for the use of less liquid and less material while achieving greater sensitivity.

In another embodiment, a wider channel is used, thereby resulting in a larger volume that can be carried on wicking device 12. However, if the same volume of liquid is used, the liquid and the material carried in the liquid will be driven to the free end of the wicking device 12, resulting in all or most of the liquid and material at or near the free end of the wicking device 12. As a result, there will be a non-uniform distribution of liquid and material along the wicking device 12.

In another embodiment, the channel 20 may be non-linear. For example, the channel 20 may branch into several side channels, the channel 20 may include one or more "t" junctions, the channel 20 may include circular path components, the channel 20 may include a square spiral path component, and the channel 20 may include other path features and combinations of features. Similarly, the wicking device 12 may also have a shape other than a uniform, linear shape along its length.

Several embodiments of the present invention will now be described to illustrate the present invention. Those embodiments are illustrative, and not limiting. Other variations and embodiments of the present invention are also possible.

Micro-Cantilever Design

Figure 3A:
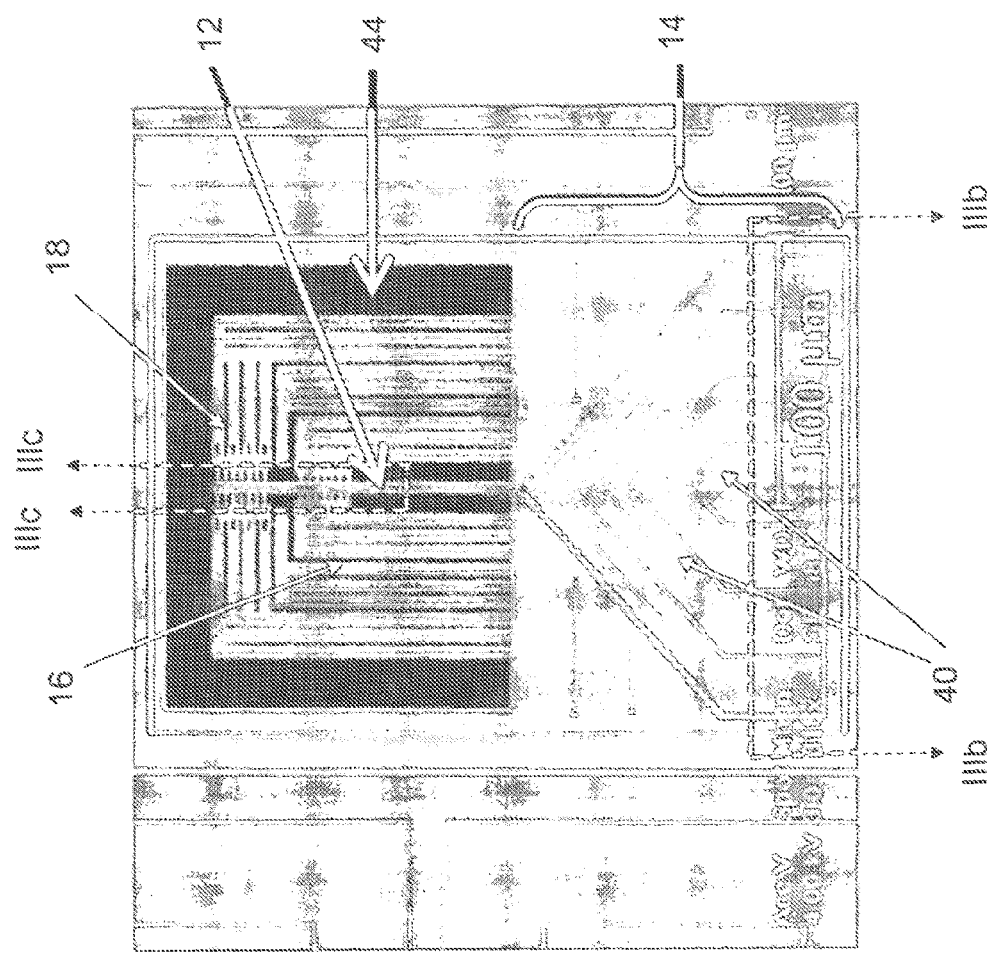
FIG. 3a illustrates one embodiment of a gravimetric micro-cantilever resonant sensor according to the present invention.
Figure 3B:
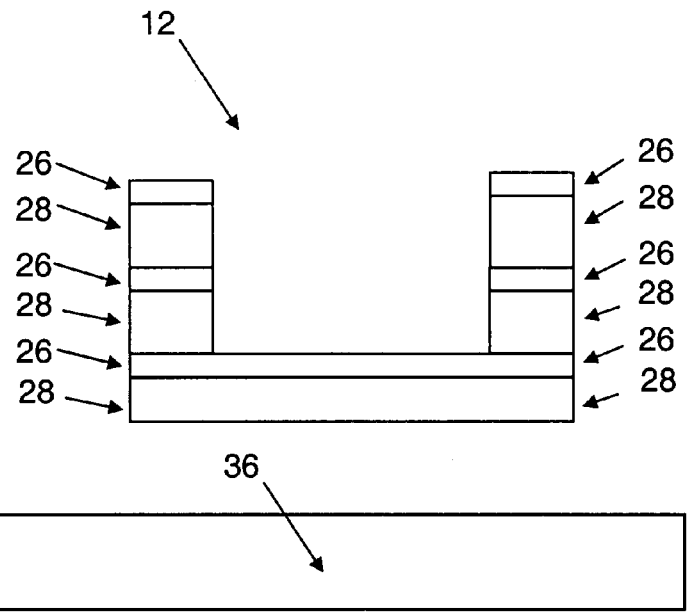
Figure 3C:
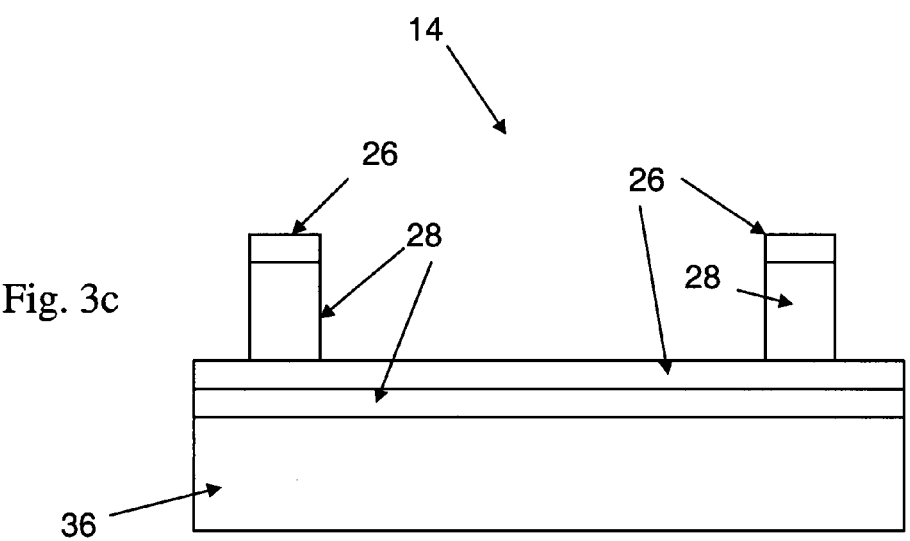
Figure 4A:
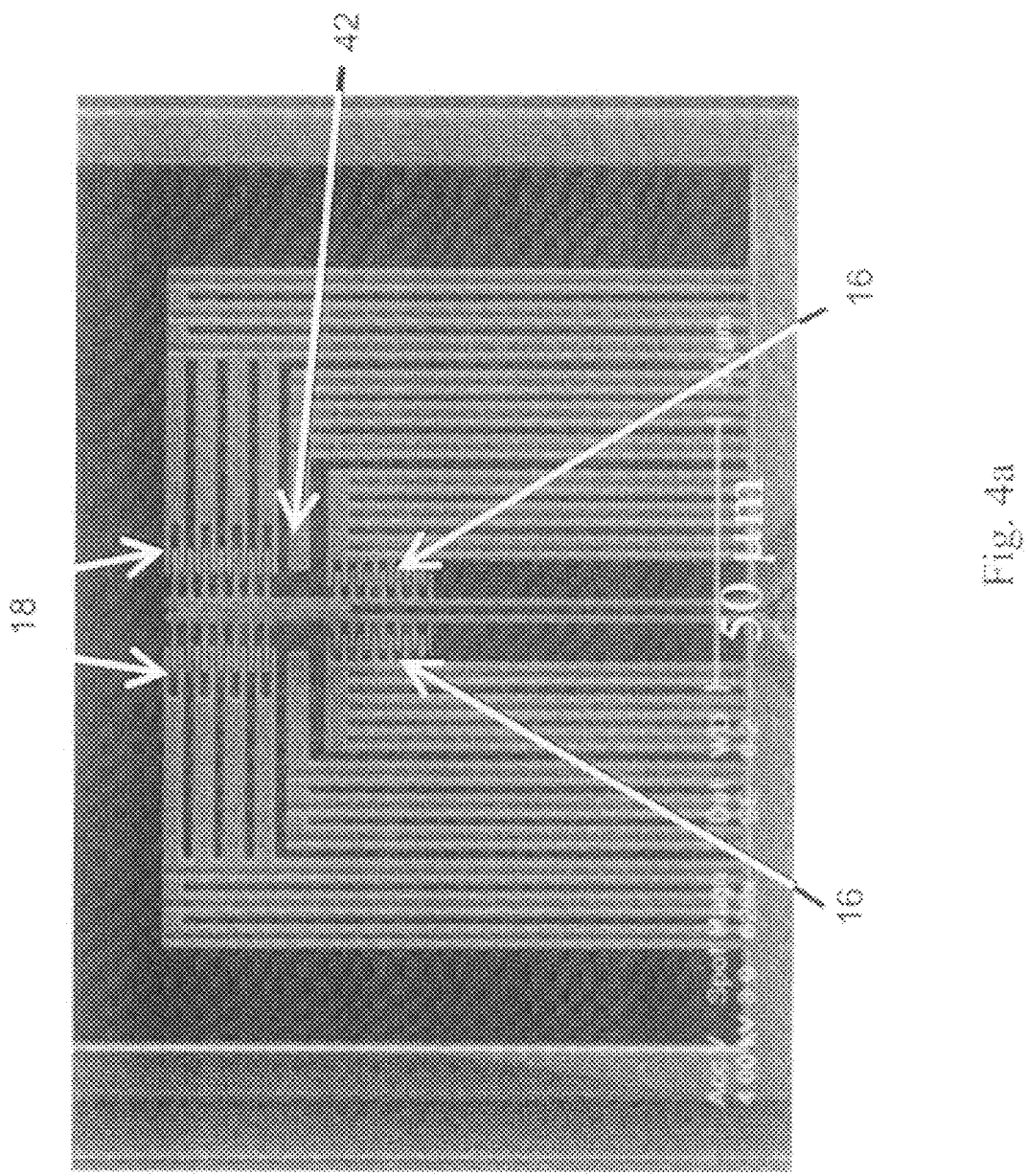

FIG. 3a is an image of an actual gravimetric micro-cantilever sensor 10 constructed according to one embodiment of the present invention. FIGS. 3b and 3c illustrate cross-sectional views along lines and respectively, in FIG. 3a. FIGS. 4a and 4b illustrate close up views of the beam microstructures forming the wicking device 12, the motion sensors 16, and the actuators 18. The reservoir or target well area 14 for solution delivery is placed at the base of the cantilevered beam 12, which is a movable structure in this embodiment.

FIG. 3b illustrates a cross-sectional view along line IIIb-IIIb of the invention illustrated in FIG. 3a. FIG. 3b shows the wicking device 12 suspended above a substrate 36. The substrate may be silicon, such as when semiconductor fabrication techniques are used to make the present invention. However, other materials and other fabrication techniques may also be used.

FIG. 3c illustrates a cross-sectional view along line IIIc-IIIc of the invention illustrated in FIG. 3a. FIG. 3c shows the fluid well 14 built on a substrate 36 and with walls made from conductive 26 and insulating 28 materials such as those used to make the wicking device 12 and described hereinabove. In other embodiments, different materials and structures may be used to form the well 14 and its associated parts.

FIGS. 4a and 4b illustrate the structure of the device including the cantilevered beam, a differential comb drive 18, and motion sensing electrodes 16. The wicking device 12 is anchored 46 at one end (see FIG. 4b), such as to a substrate, and is free to move or resonate at the other end. Ink jetting technology is used to deposit solution into the fluid well 14 which is sized to accommodate the volume of the drop emitted from the ink jet. In the illustrated embodiment the target area 14 includes grooves or ridges 40 to facilitate capillary motion of the fluid towards the groove 20 of the wicking device 12. The ridges 40 are omitted from the cross-section in FIG. 3C for simplicity.

This non-contact technology is scalable for large arrays, easy to use, faster than other means of coating such as micro capillaries and pipettes, and versatile. Other thin film application methods include dip pen and shadow mask processing which are both time consuming processes. Ink jetting is an excellent technology for functionalizing each individual cantilever separately in an arrayed structure. Although the present invention will be discussed in terms of using ink jetting, other application technologies may also be used.

In one embodiment of the present invention, the solution is deposited into the reservoir 14 and the solution is wicked into the 2 µm wide groove 20 running the length of the micro-cantilever 12, which is 4 µm wide. Once the solvent from the solution evaporates and dries, the polymer which was cast in solution is left in the 2 µm groove 20. This process of depositing polymer onto a micro-cantilever 12 is done without destruction of the device. Such a delivery system using ink-jet printing technology is significant because the approximate volume of the drop, $3 \times 10^{-14}$ m$^3$, is greater than the volume of the micro-cantilever 12, $1.4 \times 10^{-15}$ m$^3$, by more than an order of magnitude. The present invention teaches a method for depositing polymer onto a micro-cantilever 12 without destruction of the device. Polymer delivery to the cantilever 12 leads to gas chemical sensing and other applications by using a mass sensitive polymer. The combination of a sensitive layer with an electrostatically actuated cantilever 12 yields a mass sensitive detector. On chip electronics can be integrated with this mass sensor for motion detection using capacitive detection. Applications of this fabrication method may include mass sensing and chemo-resistive sensing for gas chemical detection.

In the illustrated embodiments the resonant structure 12 is a simple 120 µm-long, 4 µm-wide beam with a 2 µm-wide micro-groove 20 running along the length of the beam, although other dimensions are possible with the present invention. Motion is parallel to the surface of the silicon substrate. Differential comb drives 18 with seven rotor fingers are located near the end of the beam 12 for lateral electrostatic actuation. The stator fingers are suspended by three cantilever beams connected in parallel and sized identically to the resonator cantilever beam 12. Any curl from vertical stress gradient is matched to ensure the stator 18 and movable comb fingers are aligned in the same plane. Motion sensing of the plate is implemented using capacitive comb electrodes 16 placed on both sides of the main beam 12 and located further toward the base from the actuation combs. A limit stop 42 is located between the actuator 18 and sense combs of the motion sensor 16. The beam 12, sensors 16, actuators 18, limit stops 42, and their associated structures are suspended over a silicon etch pit 44.

A target well 14 area is located at the base of the cantilever 12 to collect the jetted drops. The well 14 has an approximate depth of 9 µm and a maximum width of 165 µm. The well 14 narrows in width toward the base of the cantilever 12 at a 45° angle on each side. Other sizes and shapes are also possible for the target well 14 area.

Although FIGS. 3a, 3b, 3c, 4a, and 4b illustrate a single apparatus 10, the present invention may include multiple apparatuses 10 in a single device or on a single substrate. For example, multiple apparatuses 10 may be used to perform redundant tests to ensure accuracy. Alternatively, different apparatuses 10 may perform different tests to provide a wide variety of information. As a result, a single device may contain a single apparatus 10, or it may contain multiple apparatuses in which there are several versions of the same apparatus 10, or in which there are several different apparatuses 10. The apparatuses 10 may, for example, receive the same material in their respective target wells 14, or they may receive different materials. For example, these different materials can be different polymers each with different mass sensitivity to various gas chemical analytes.

Figure 5:
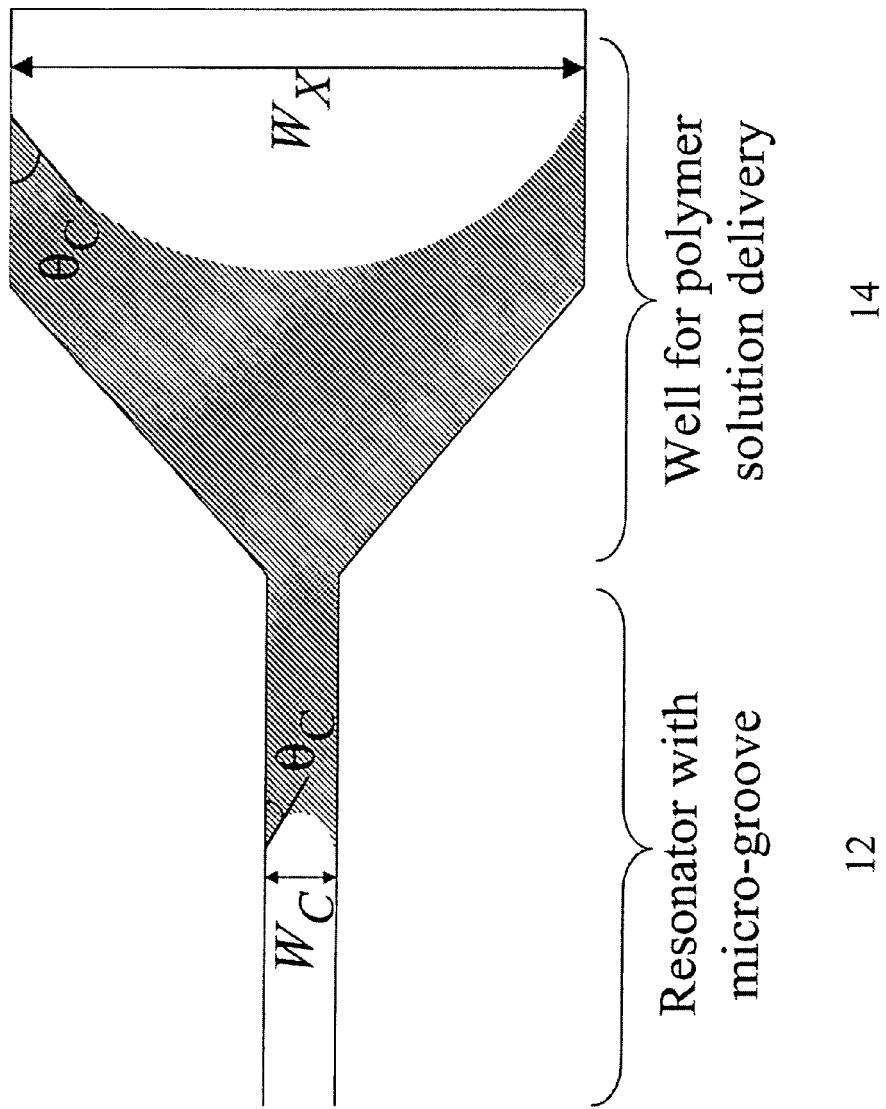
FIG. 5 illustrates one embodiment of a solution delivery to the resonator.

FIG. 5 illustrates a schematic of the transition region between the well 14 and the groove 20. A pressure difference exists between the two surfaces of the liquid/gas interface (R. Aoyama, M. Seki, J. W. Hong, T. Fujii, and I. Endo, "Novel Liquid Injection Method with Wedge-Shaped Microchannel on a PDMS Microchip System for Diagnostic Analyses," Journal of MEMS, p. 1232, (2001)). This differential pressure is:

$$\Delta P_{XC} = 2\gamma \cos\theta_C \left(\frac{1}{W_X} - \frac{1}{W_C}\right) \quad (1)$$

where $\gamma$ is the surface tension, $\theta_C$ is the contact angle, $W_X$ is the width of the well and $W_C$ is the width of the micro-groove 20 running along the length of the cantilever 12. This causes a flow of the solution by capillary action from the well 14 to the resonator 12. Once the solvent dries polymer is left in the micro-channel in the resonator 12.

Oscillator Design

Figure 6:
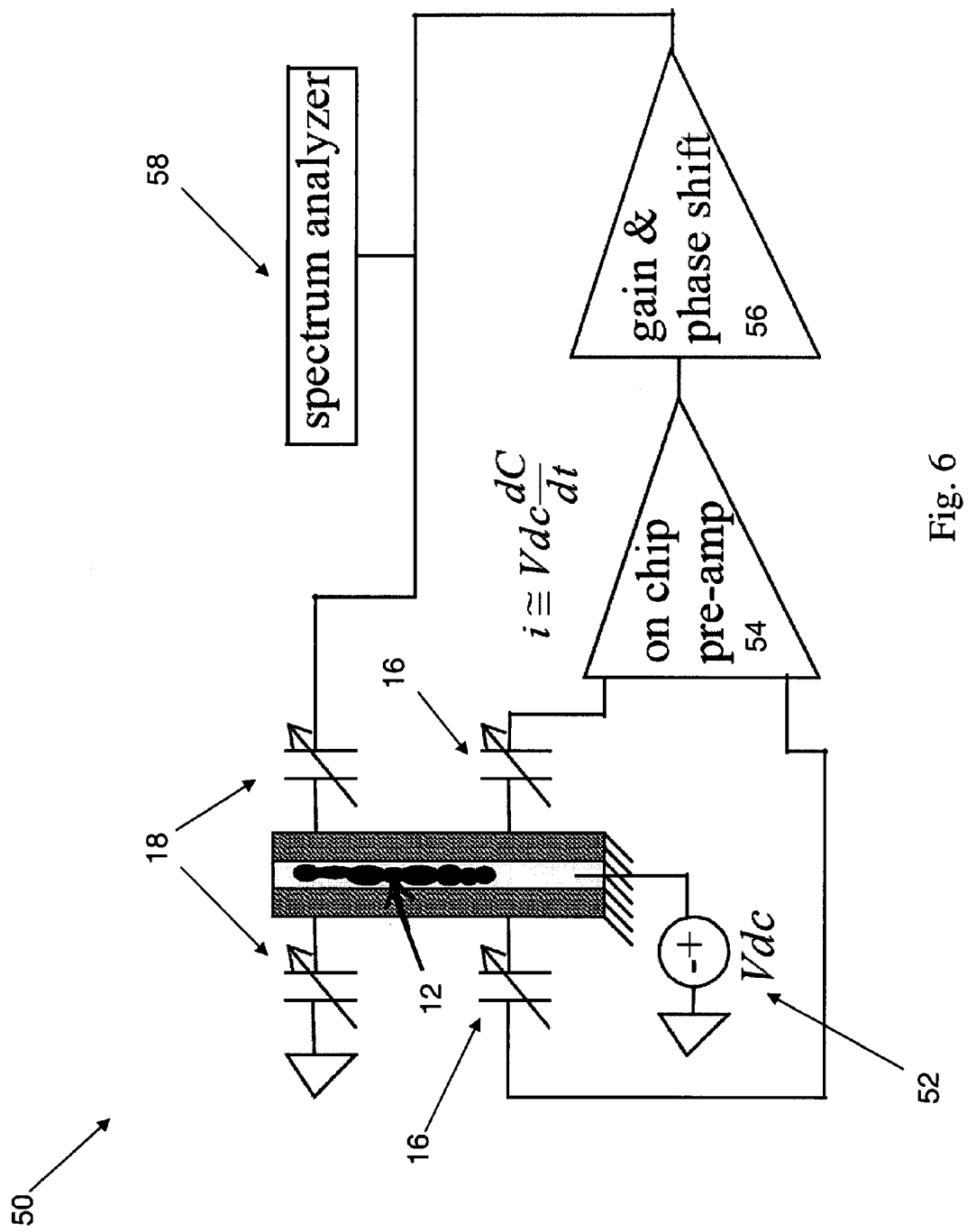
FIG. 6 illustrates one embodiment of an oscillator gas sensor schematic. The electrostatically actuated resonator is placed in a feedback loop with off-chip electronics for oscillation.

FIG. 6 illustrates a block diagram of the closed-loop feedback system 50 to sustain the resonant oscillation. A dc polarizing voltage, $V_{dc}$ 52, is applied to the movable beam 12. The resonator velocity is detected by measuring the motional displacement current, $V_{dc}$ dC/dt, through the comb finger capacitors. An on-chip preamplifier 54 produces a voltage, $V_s$, that is proportional to the difference of the current through the differential capacitors formed by the sense comb electrodes.

An external amplifier 56 placed in series with the on-chip pre-amplifier 54 provides 40 dB of gain and −90° of phase shift at the mechanical resonance. This phase compensation is needed for free running oscillation. In this implementation, only one side of the differential actuator is used. During free oscillation, the actuator voltage amplitude is 0.2 V with a dc polarizing voltage of 23.0 V. A spectrum analyzer 58 is used to monitor the output of the amplifier 56 and determine differences in the resonance frequency of the device movable beam 12.

The calculated resonant frequency from layout dimensions and prior to polymer deposition is 250 kHz. With analyte addition, a change in the mass of the cantilever 12 changes the resonance frequency. The mass sensitivity (gm/Hz) is:

$$\frac{\Delta m}{\Delta f} = -\frac{4\pi(m_b + m_{poly})^{\frac{3}{2}}}{\sqrt{k}} = -\frac{2(m_b + m_{poly})}{f_o} \quad (2)$$

where $m_b$ is the mass of the beam, $m_{poly}$ is the mass of the polystyrene or other material being measured, k is the spring constant of the cantilever, and $f_o$ is the resonance frequency of the cantilever 12. The calculated mass sensitivity for this device is 76 fg/Hz. The sensitivity (Hz/ppm) of the microbalance due to analyte concentration is calculated as follows (see, S. S. Bedair and G. K. Fedder, "CMOS MEMS Oscillator for Gas Chemical Detection," Proceedings of IEEE Sensors, Vienna, Austria, Oct. 24-27, 2004):

$$\frac{\Delta f}{\Delta C_{air}} = \frac{\Delta f}{\Delta m}\frac{\Delta m}{\Delta C_{air}} = -\frac{f_o}{2(m_b + m_{poly})} K_{PG} V_{poly} \quad (3)$$

where $C_{air}$ is the concentration of the analyte in air, $K_{PG}$ is the partition coefficient associated with the particular polymer/analyte combination, and $V_{poly}$ is the volume of the polymer on the beam 12. The volume of polymer to fill the micro-groove 20 is $7.2 \times 10{-16}$ m$^3$. Assuming that the micro-groove 20 is filled with polystyrene the concentration sensitivity to ethanol, 2-propanol, and acetone is calculated to be 0.006 Hz/ppm, 0.005 Hz/ppm, and 0.01 Hz/ppm, respectively. Other materials will result in a different sensitivity of the device 10.

Fabrication

Figure 7:
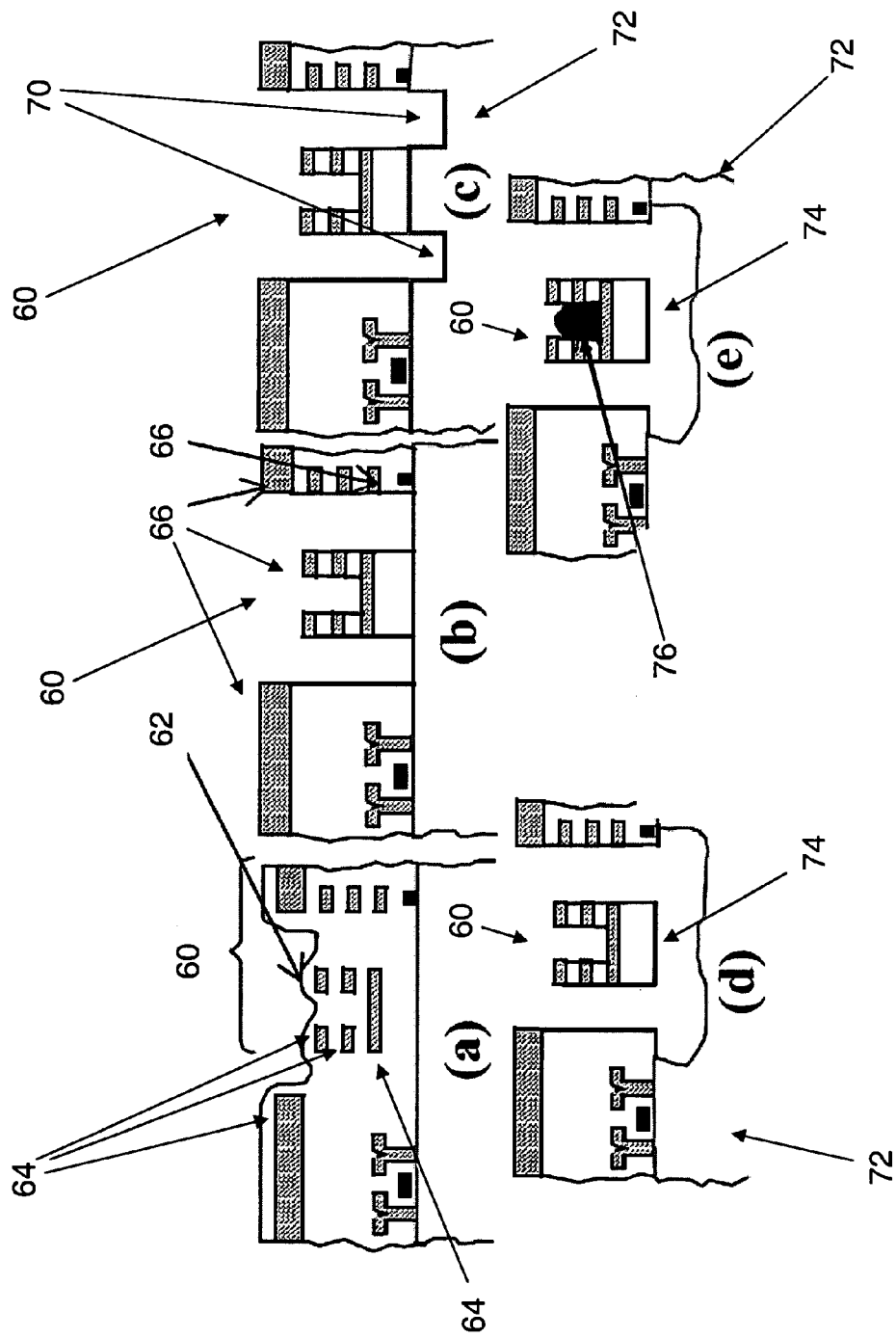
FIG. 7 illustrates one embodiment of post CMOS processing steps: (a) CMOS chip from foundry, (b) Reactive-ion etch of dielectric layers, (c) DRIE of silicon substrate, (d) isotropic etch of silicon substrate, (e) Ink jet deposition of polymer solution.

FIG. 7 illustrates one method of fabricating a sensor 10 according to the present invention. The sensor 10 was fabricated in the SiGe 0.35 µm BiCMOS technology from Jazz Semiconductor (Newport Beach, CA) followed by post-CMOS micromachining (G. K. Fedder, S. Santhanum, M. L. Reed, S. C. Eagle, D. F. Guillou, M. S. C. Lu, and L. R. Carley, "Laminated high-aspect-ratio microstructures in a conventional CMOS process," Proceedings of the 9th IEEE International Workshop on Micro Electro Mechanical Systems (MEMS '96), San Diego, Calif., Feb. 15-17, 1996, pp. 13-18). As illustrated in FIG. 7(a), the structures 60 that will form the sensor are embedded in silicon oxide-based layers 62 or other material used in the fabrication process. Metal interconnect layers 64 are also present.

After foundry CMOS fabrication, three dry etch steps are used for definition and release of the structures 60, as illustrated in FIG. 7(b). The intermetal dielectric layers are etched using an anisotropic $CHF_3/O_2$ reactive-ion etch (RIE) (FIG. 7(b)) where the top metal layer 66 acts as a mask defining the pattern of the structure. A subsequent undercutting of the structures 60 by a Si etch is performed using an anisotropic deep reactive-ion etch (DRIE) to form a recess 70 in the bulk silicon 72 (FIG. 7(c)) followed by an $SF_6/O_2$ isotropic etch (FIG. 7(d)) of the bulk silicon 72 to form the undercut 74 of the structures 60 for structural release of the metal and dielectric stack 60. In the illustrated embodiment, the sidewalls and bottom of the micro-grooves are defined by the metal-3 and metal-1 layer, respectively, in the CMOS technology.

In FIG. 7(e) the chemically sensitive polymer dissolved in solvent 76 is deposited using a piezoelectric drop-on-demand ink jet purchased from MicroFab Technologies (Plano, Tex.). The orifice of the ink jet is 30 μm in diameter and the average drop size is 31 μm in diameter. An x-y stage (Aerotech Inc.) that moves the device under the ink jet provides positional accuracy of 0.2 μm.

Although the present invention has been described in terms of one embodiment with regard to FIGS. 7(a)-7(e), other variations and modifications are also possible with the present invention. For example, different devices, such as different types of sensors as well as devices other than sensors, may be used with the present invention. Similarly, other structures and other materials may be used with the present invention. In addition, other processes and technologies, such as other micromachining and nanomachining processes and technologies may also be used to manufacture apparatuses according to the present invention.

Polymer Delivery Results

Figure 8:
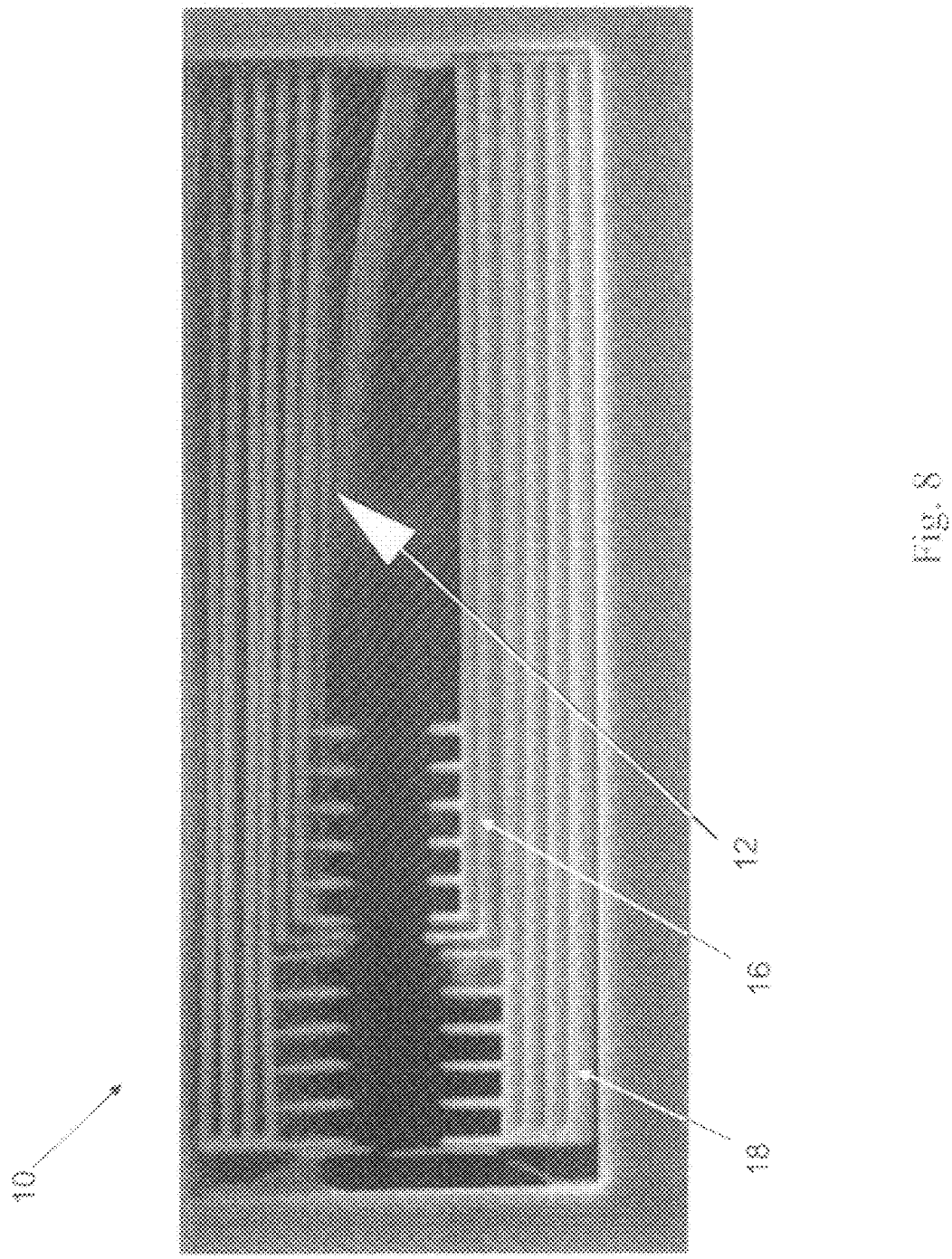
FIG. 8 illustrates an example of a beam pinned under stator electrodes after direct ink jet deposition onto cantilever.

FIG. 8 illustrates an attempt to directly deposit material onto a cantilever wicking device 12. Polymer deposition tests used two mg/mL polystyrene mixed in a 1:1 mixture of HPLC grade toluene and xylene at room temperature. The solution was then sonicated for ten minutes.

As expected, attempts to directly deposit onto the cantilever 12 result in the destruction of the device 10. This occurs because the ink-jetted drop volume (~33 pL) greatly exceeds the target cantilever 12 size. The wicking device 12 is pinned under the actuating electrodes 18 due to surface tension effects rendering it inoperable. In addition, the deposited material covers both the cantilevered wicking device 12 and surrounding structures, such as actuators 18 and motion sensors 16. As a result, even if the wicking device 12 were to remain in, or be returned to, a functioning state, the apparatus 10 would not function because other parts of the apparatus 10 are covered in the material that was supposed to be deposited only on the wicking device 12.

Figure 9:
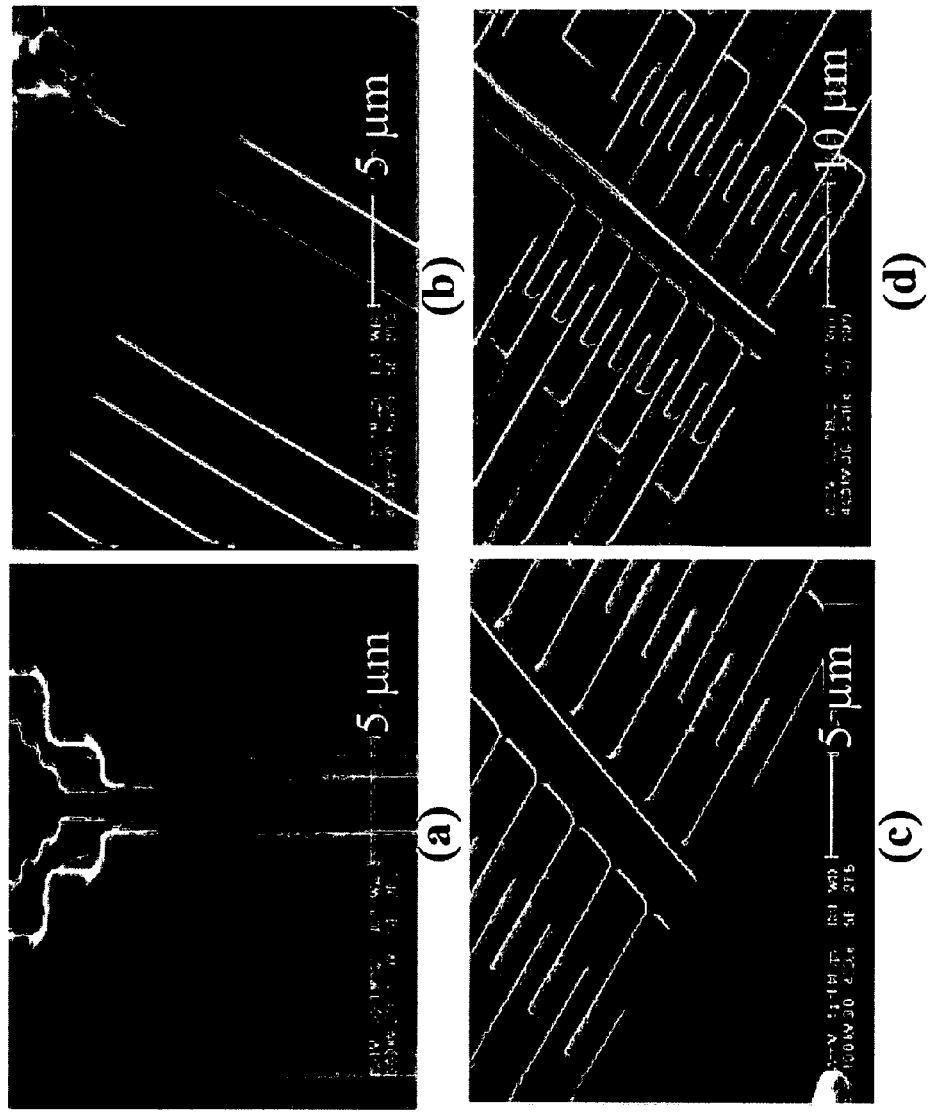
FIG. 9a-9d illustrate one embodiment of a device before and after solution deposition in the well:(a) entrance from well to micro-channel which extends along the length of the resonator, (b) resonator at the base with polystyrene, (c) tip of resonator without polystyrene, (d) tip of resonator with polystyrene.
FIG. 9e illustrates frequency response of one embodiment of a device before and after polystyrene deposition into a 2 μm channel in the device.

FIGS. 9a-9d illustrate loading material onto the cantilever 12 according to the present invention. In that example, six drops of solution (two mg/mL polystyrene in 1 toluene:1 xylene) were deposited onto the target area at the base of the cantilever beam 12. The polymer wicks onto the cantilever beam 12 and the solvent then evaporates. A view at the base of the cantilever micro-channel 20 is shown in FIG. 9(a) and FIG. 9(b) before and after polystyrene deposition, respectively. The tip of the micro-channel resonator 12 with and without polystyrene is shown in FIG. 9(c) and FIG. 9(d), respectively. The device was successfully operated with electrostatic actuation.

Figure 9E:
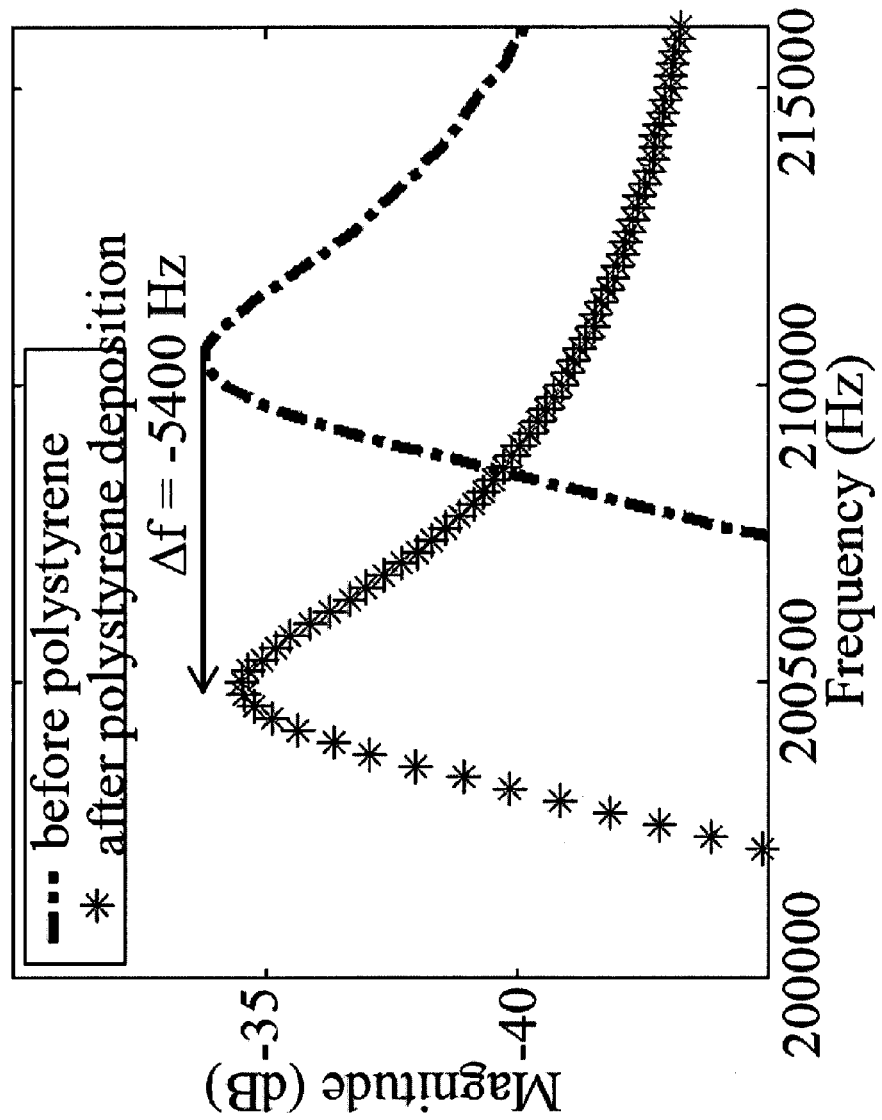

FIG. 9e illustrates the frequency response of the cantilever 12 before and after polystyrene loading. The resonance frequency shifted down by 5400 Hz. This corresponds to an added polymer mass of 410pg. The calculated mass of polystyrene in six drops of solution is 396 pg.

FIG. 10a-10g are scanning electron micrographs ("SEM") illustrating several embodiments of the present invention after material deposition. In these embodiments, the material deposited is a polymer, although other materials may also be used with the present invention.

FIG. 10a is a top view SEM after polymer deposition. FIG. 10b is a cross-sectional view along line Xb-Xb in FIG. 10a. FIG. 10b shows material at the tip of the wicking device 12 after polymer deposition. FIGS. 10a and 10b illustrate an embodiment of the present invention in which the channel 20 is a vertical slot type channel, having a channel width and height of 1.5 μm and 3.2 μm, respectively.

Figure 10D:
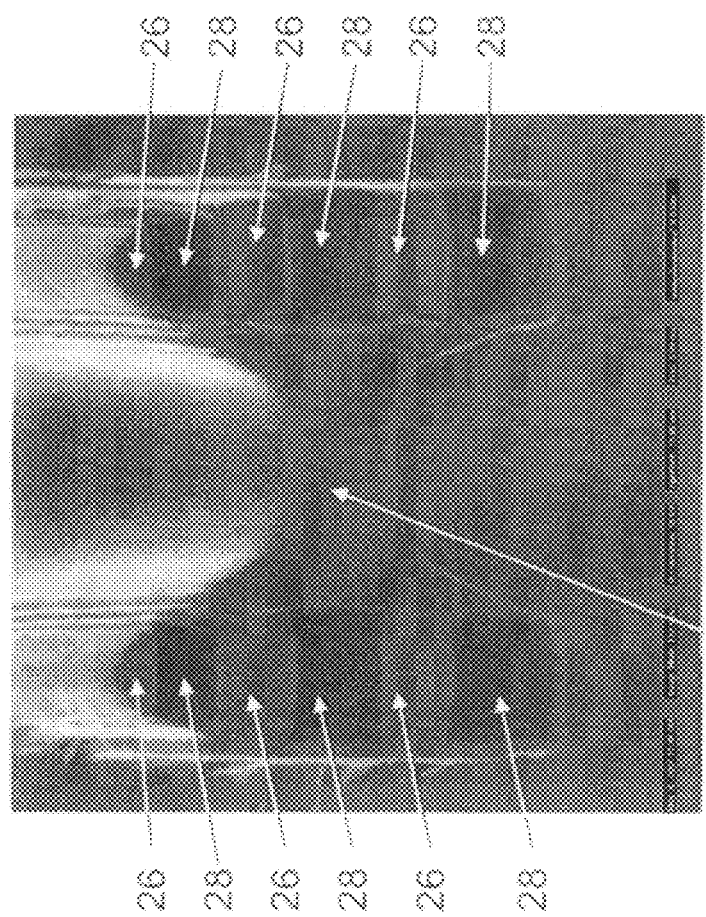
Figure 10C:
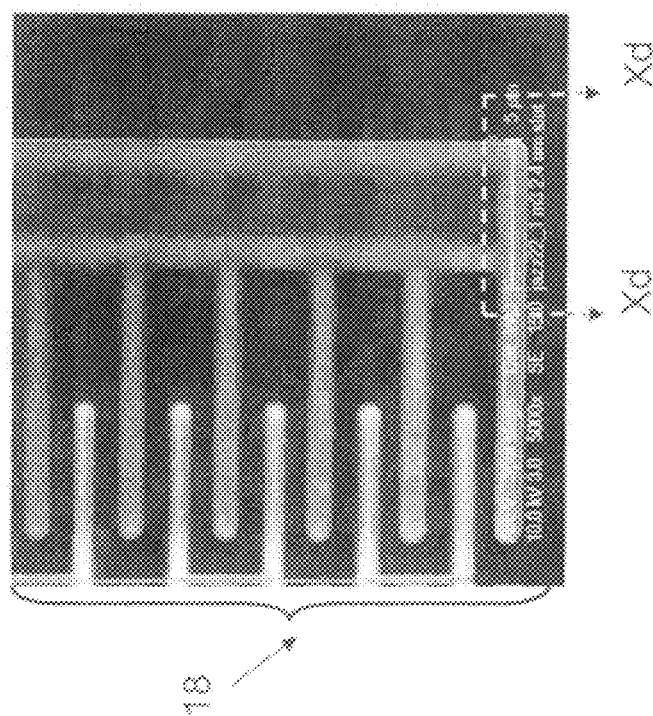

FIG. 10c is a top view SEM after polymer deposition of another embodiment of the present invention. FIG. 10d is a cross-sectional view along line Xd-Xd in FIG. 10c. FIG. 10d shows material at the tip of the wicking device 12 after polymer deposition. FIGS. 10c and 10d illustrate an embodiment of the present invention in which the channel 20 is a vertical slot type channel, having a channel width and height of 2.4 μm and 4.8 μm, respectively.

FIG. 10e is a top view SEM after polymer deposition of another embodiment of the present invention. FIG. 10f is a cross-sectional view along line Xf-Xf in FIG. 10e. FIG. 10f shows material at the tip of the wicking device 12 after polymer deposition. FIGS. 10e and 10f illustrate an embodiment of the present invention in which the channel 20 is a vertical slot type channel, having a channel width and height of 2.8 μm and 4.8 μm, respectively.

Figure 10G:
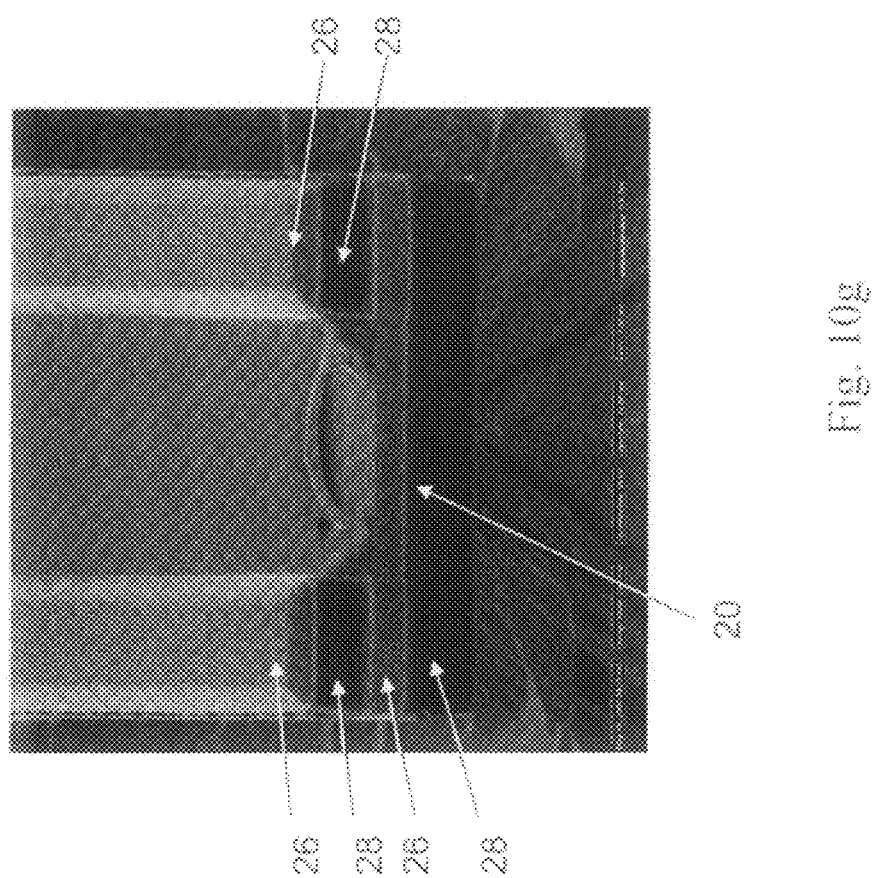

FIG. 10g is a cross-section view of the tip of a wicking device 12 after polymer deposition. The channel 20 in the wicking device 12 is a vertical groove type. The channel width and height are 1.5 μm and 3.5 μm, respectively.

Gas Test Measurements

Figure 11:
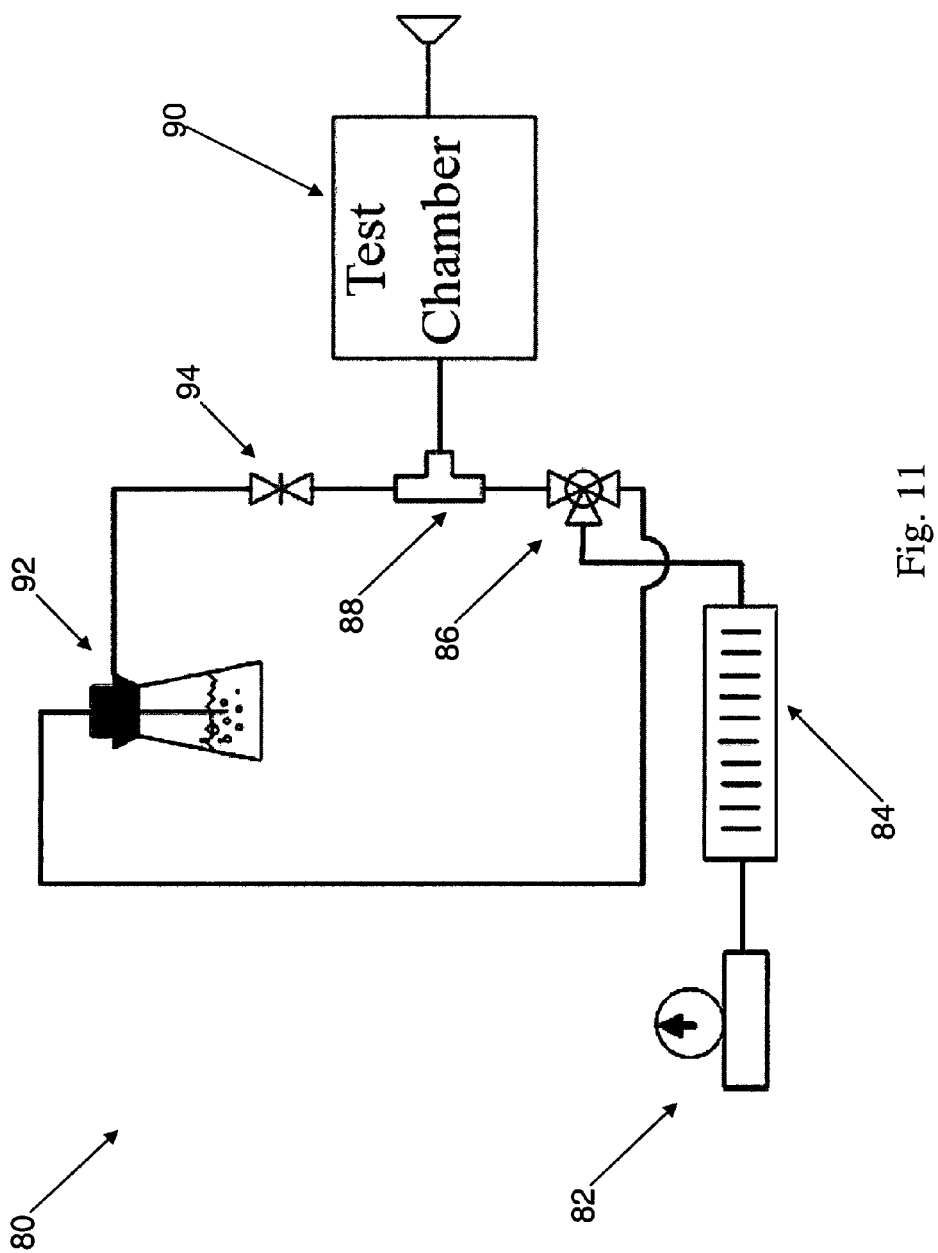
FIG. 11 illustrates one embodiment of a gas test setup according to the present invention.

FIG. 11 illustrates a gas test system 80 according to one embodiment of the present invention. Gas analytes are introduced with nitrogen as the carrier gas. The nitrogen supply 82 is connected through an adjustable flow-meter 84 and a 2-way ball valve 86. The flow-meter 84 has a minimum flow rate of 0.21 liters per minute (Lpm) and a maximum rate of 1.21 Lpm. One outlet of the ball valve 86 connects to a T-connector 88 for direct connection of the carrier gas and analyte vapor to the test chamber 90. The other outlet of the ball valve 86 is connected to the inlet of a bubbler 92 which is submersed in the liquid form of the analyte of interest. The outlet of the bubbler 92 is connected to the through a valve 94 and the T-connector 88 to the test chamber 90.

Tests were performed with ethanol, 2-propanol, and acetone. $N_2$ was flowed at 1 Lpm through the chamber using an external bubbler until an equilibrium concentration is reached. In these initial tests, the equilibrium concentration was not measured but is assumed to be at or close to the saturation concentration of the corresponding vapor at a temperature of 300 K and a pressure of 1 atm.

Figure 12:
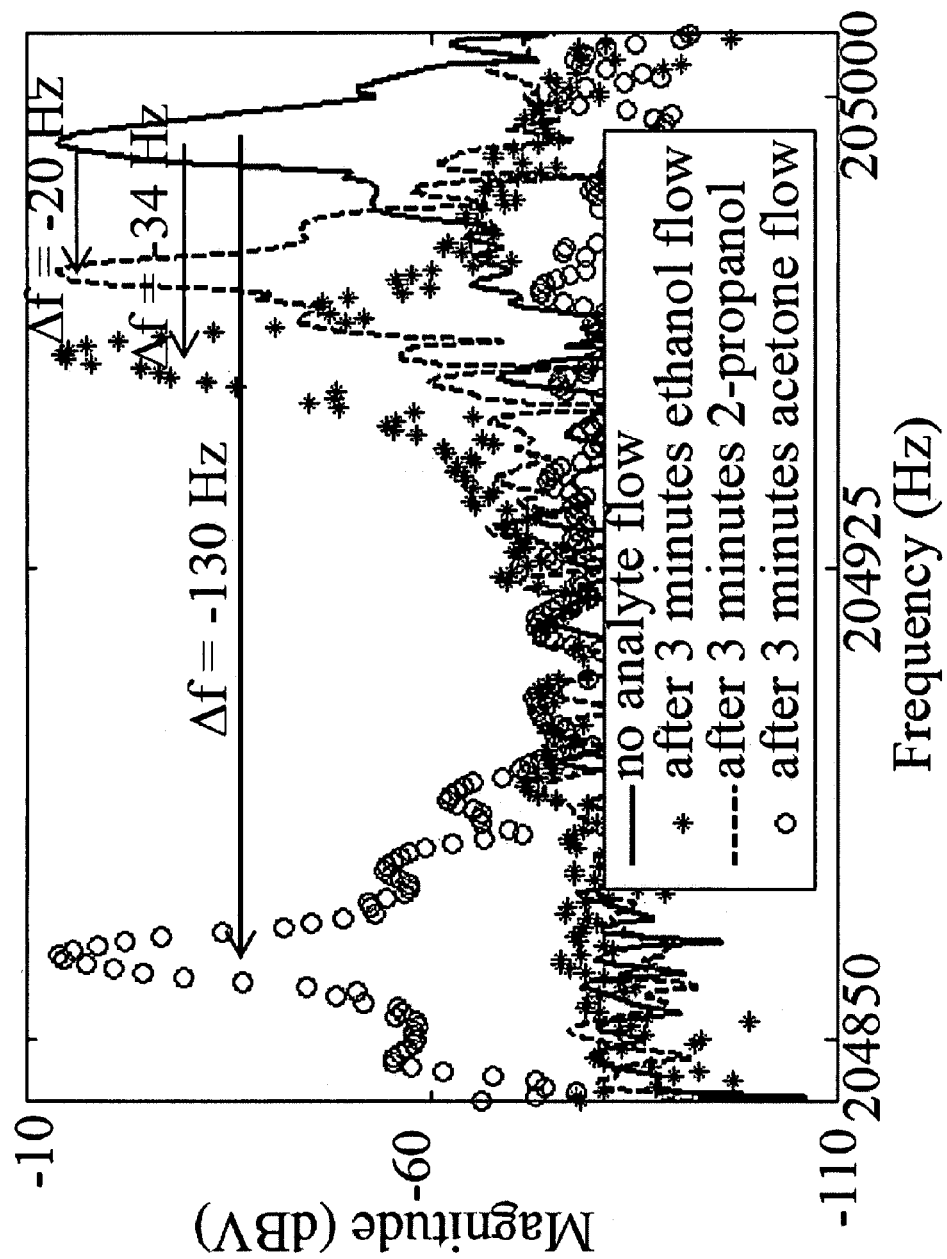
FIG. 12 illustrates spectrum analyzer output of resonant frequency shifts due to ethanol, IPA, and acetone gas flows according to one embodiment of the present invention.

FIG. 12 illustrates the free-running oscillator responses to ethanol, 2-propanol, and acetone flows. The mechanical resonance frequency with no exposure to analyte is 204.499 kHz. The oscillator signal has a 65 dB SNR and a 3 dB width of 3 Hz limited by the 3 Hz resolution bandwidth of the spectrum analyzer. From the frequency shifts in FIG. 12, the amount in grams of ethanol, 2-propanol, and acetone loaded into the polystyrene is calculated to be approximately 1.5 pg, 2.6 pg, and 9.9 pg, respectively.

Conclusions

The gas tests successfully demonstrate an organic vapor detector using the CMOS-MEMS self-excited resonator oscillator. The polymer loading method that exploits capillary action in the micro-groove enables design of narrow-gap electrostatic combs alongside the micro-cantilever. Compatibility with ink jet polymer delivery enables loading of different polymers to individual cantilever sensors. The precise amount of polymer loading with this method should lead to repeatable results from device to device.

Scaling down the cantilever size led to a high mass sensitivity of 76 fg/Hz for the 4 μm-wide cantilever design. With further design maturation, further device scaling and incorporation of further materials onto the wicking devices on the cantlivers, the technology should lead to highly sensitive gas chemical gravimetric sensor arrays on chip.

Other Embodiments

FIGS. 13a and 13b illustrate another application of the present invention in which one or more channels 20 are used to provide an adhesive to secure a first object 100 to a second object 102. In FIG. 13a, the first 100 and second 102 objects are apart and a force 104 presses them together. In FIG. 13b, the first 100 and second 102 objects are together, and one or more channels 20 in the second object 102 are used to carry adhesive to an interface between the first 100 and second 102 objects. After the adhesive dries the first 100 and second 102 objects are bonded together.

This application of the present invention may be used, for example, to assemble parts, such as parts used to create microelectromechanical systems, or other parts. In the illustrated embodiment, the first object 100 includes offsets or stops 106 which engage the second object 102 and provide for a predetermined spacing or gap 108 between the first 100 and second 102 objects. This may allow, for example for very small and/or very precise gaps or spaces to be formed.

Narrow gaps, for example, smaller than possible with conventional photolithographic techniques, with electrodes at either side of the gap are of interest for providing high electrostatic forces and high capacitance sensitivity. In other embodiments, stops 106 may be omitted, and two or more parts may be assembled in different orientations. Many other variations and modification are possible with this application of the present invention.

Figure 13D:
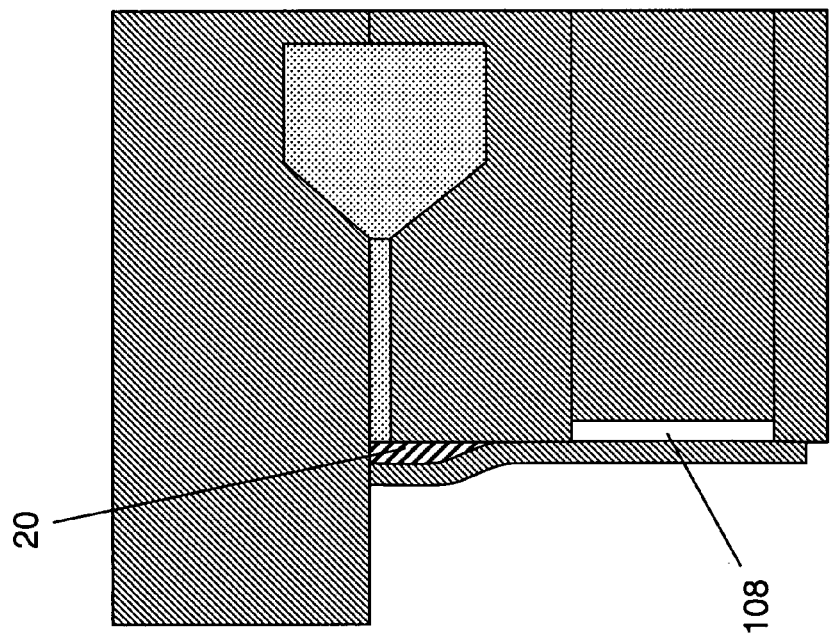
FIGS. 13c and 13d illustrate another embodiment of the present invention in which a suspended beam is used for form a space or gap.
Figure 13C:
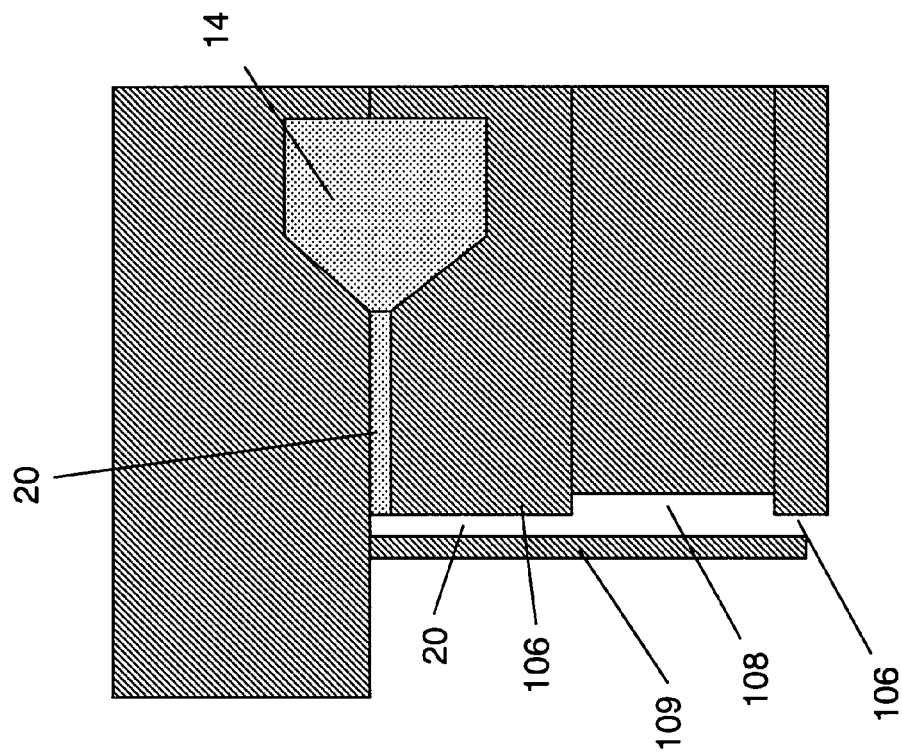

FIGS. 13c and 13d illustrate another embodiment of the present invention in which material, such as an adhesive, is deposited in the well 14 and wicked through the channel 20. Part of the channel is defined by a moveable beam 109. When the material flows through the portion of the channel 20 formed by the moveable beam 109, the surface tension of the material causes the beam 109 to bend inward. If the material is an adhesive, it will dry and fix the beam 109 in that position.

In the illustrated embodiment, the bent beam 109 engages stops 106 limiting the motion of the beam and forming a space or gap 108.

Figure 14:
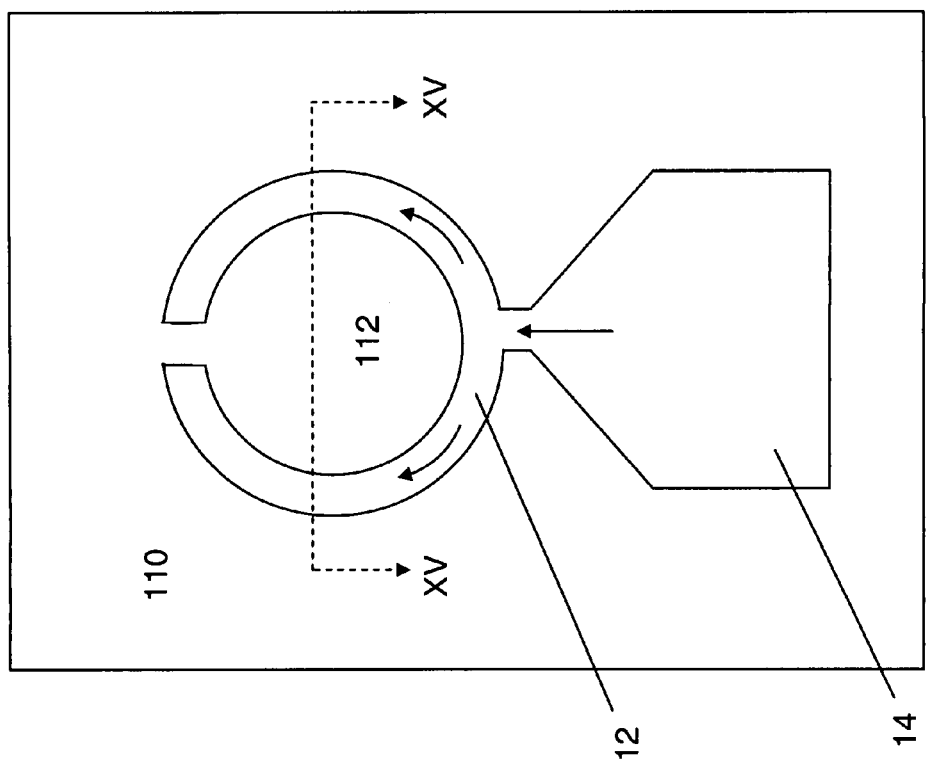
FIGS. 14 and 15 illustrate another embodiment of the present invention in which parts of an object or layer are joined with a material according to the present invention.

FIG. 14 illustrates another application of the present invention in which the channel 12 is an opening or void in an object or layer 110. In the illustrated embodiment, the channel 20 defines a circular portion 112 within the larger object 110. In this embodiment, an adhesive or other material is provided in the fluid well 14, from which the material flows into the channel 20 and fills the channel 20. The material filling the channel 20 may be flexible and allow for relative movement between the circular portion 112 and the larger object, or it may have some other function. Many different shapes 114 and other variations of this embodiment may be practiced with the present invention.

Figure 15:
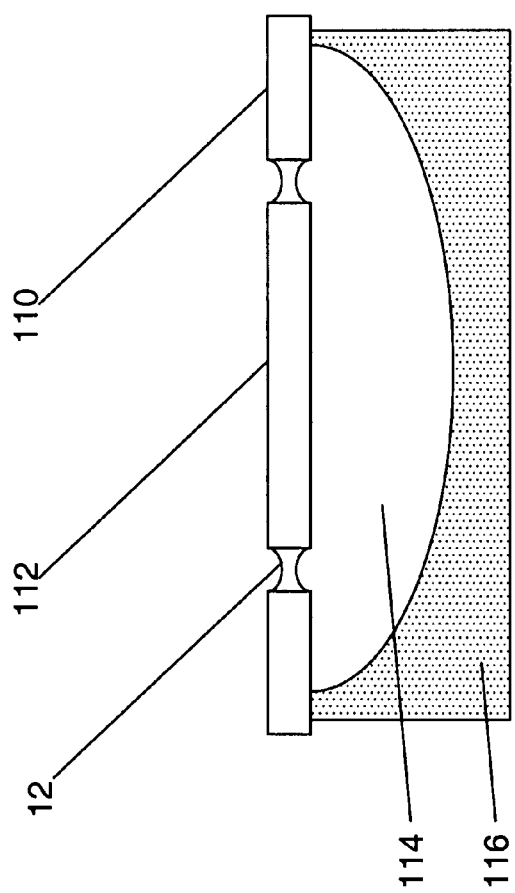

FIG. 15 illustrates a cross-section view along line XV-XV of the apparatus illustrated in FIG. 14. The two portions 110, 112 of the top layer are joined by the material in the channel 20.

In this embodiment, an opening 114 exists below the two portions 110, 112 of the top layer and a lower layer 116, although it is not required for an opening 114 to exist below the two portions 110, 112 of the top layer. The material filling the channel can be used to seal the opening 114 from the outside ambient. For example, this sealing can be used to keep liquids from entering area 114, or can be used to seal liquids inside area 114.

Figure 16:
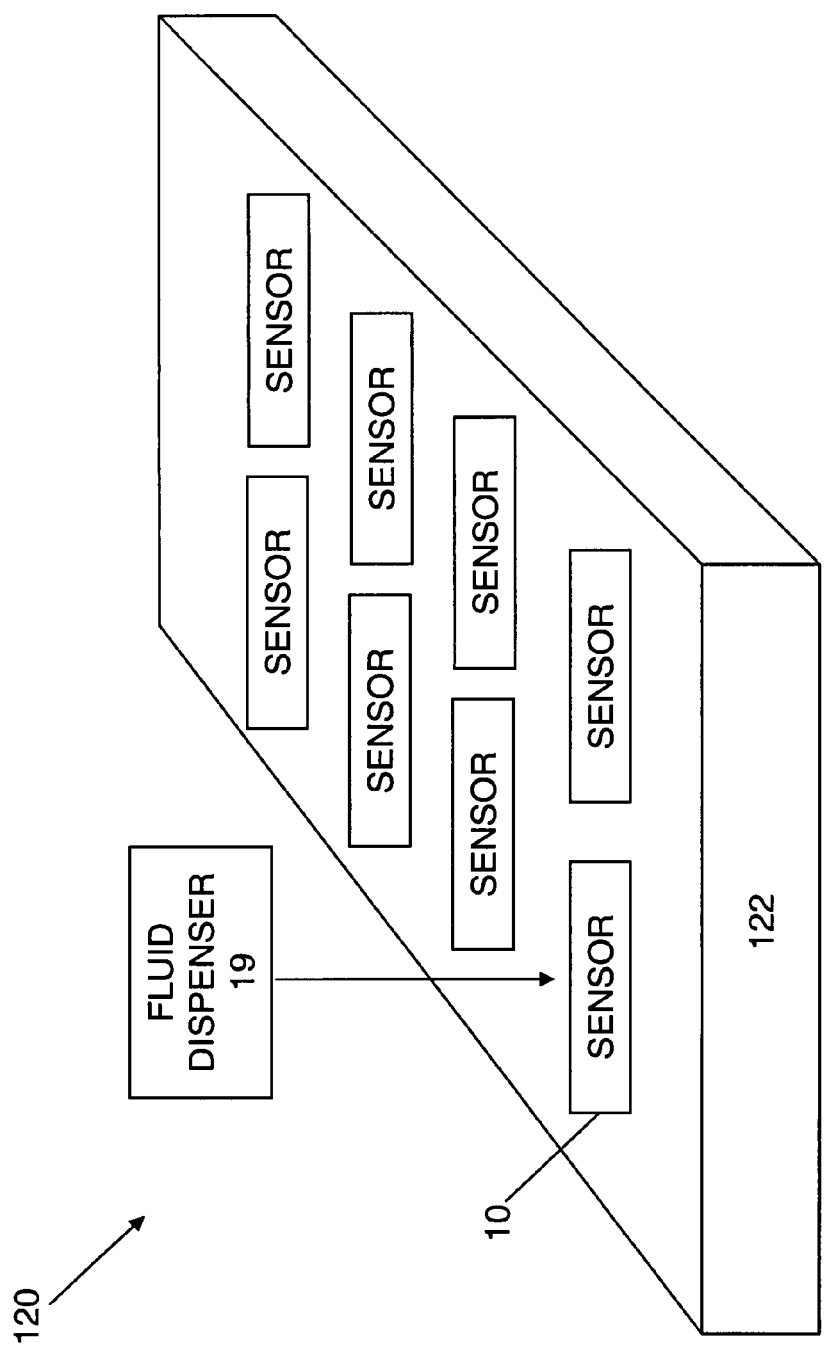
FIG. 16 illustrates one embodiment of a system according to the present invention.

FIG. 16 illustrates a system 120 according to the present invention. In that embodiment, several apparatuses 10, such as that illustrated in FIG. 1, are on a single substrate 122 or material. FIG. 16 illustrates the apparatuses 10 as being "sensors", although any apparatus 10, or any combination of different types of apparatuses, may be formed in this manner. Accordingly, the present invention allows for a large number of apparatuses to be made or used as part of a single system 120 or unit. In some embodiments, the apparatuses 10 may all be the same, such as to perform the same test multiple times on the same or different samples. In other embodiments, the apparatuses may be different, such as to provide for a variety of functions from a single system 120.

Many variations and modifications are possible with the present invention. For example, the present invention may be used in the operation of sensors. The present invention may be used to fill a space between, or to connect, two or more parts. In some embodiments, the present invention may be used to carry an adhesive to a desired location to fix two or more parts together. In other embodiments the present invention may be used to provide a dielectric between two or more electrodes or contacts. In another embodiment, the present invention may be used in a chemo resistor device in which electrically resistive material is positioned between two or more electrodes or contacts. In another embodiment, the present invention may be used as an electrostatic actuator. The present invention may also be used with a mass sensor for gas chemical sensing applications. The present invention may also be used with other fluids and materials and in other applications, such as chemo-resistive fabrication and devices, chemo-capacitive fabrication and devices, applying adhesives for capping or otherwise connecting devices, and other applications. In addition, different materials and structures may be used with the present invention. For example, some embodiments are described in terms of particular materials, although different materials may also be used. Similarly, some of the embodiments herein show a particular number and orientation of material layers used to create the various parts of the present invention. Those examples are illustrative and not limiting, and different numbers and orientations of layers may be used with the present invention. Those and other variations of the present invention are possible.

The present invention may also include two or more devices formed in a single apparatus or on a single substrate. The single apparatus or substrate may contain several devices of the same type, or it may contain different types of devices. In some embodiments, the devices receive different materials in their respective target areas, and in some embodiments they receive the same materials. As a result, different testing, sensing, or other functions may be performed on a single structure.

These and other variations and modifications of the present invention are possible and contemplated, and it is intended that the foregoing specification and the following claims cover such modifications and variations.

The invention claimed is:

1. An apparatus, comprising:
   a body containing a fluid well designed and configured to receive a fluid; and
   a structure exposed to an ambient environment capable of supporting partial evaporation of the fluid, said structure having:
   a longitudinal axis;
   a first end connected to said body;
   a second end spaced from said first end along said longitudinal axis; and
   a length from said first end to said second end;
   said structure containing a channel that extends along said length and defines a space that is in fluid communication with said fluid well and that receives a portion of the fluid from said fluid well, said channel:
   being dimensioned so as to wick the fluid from said fluid well, via capillary action, into said space along said length from said first end substantially to said second end; and
   having an opening extending at least a substantial portion of the entirety of said length of said structure so that, when 1) said structure is exposed to the ambient environment, 2) said space in said channel is in fluid communication with the space is full of the fluid, and 3) the structure is exposed to the ambient environment, said opening allows a portion of the fluid to evaporate from said space through said opening directly into the ambient environment in a direction radial to said longitudinal axis along substantially the entirety of said length;
   wherein:
   said structure comprises a pair of spaced members extending along said length parallel to said longitudinal axis, said pair of spaced members together defining said space of said channel and each having lateral sides spaced from one another and extending parallel to said longitudinal axis, said space being in fluid communication with the ambient environment along said lateral sides at a cross-section transverse to said longitudinal axis; and
   each of said pair of spaced members are cantilevered from said body.

2. The apparatus according to claim 1, wherein said pair of spaced members are connected by at least one support extending between said pair of spaced members within said channel.

3. The apparatus according to claim 1, wherein at least one of said pair of spaced members includes at least one opening exposing said channel to the ambient environment.

4. The apparatus according to claim 1, wherein at least one of said pair of spaced members comprises multiple layers.

5. The apparatus according to claim 1, wherein each of said pair of members includes an electrode and an insulator located between said electrode and said channel.

6. The apparatus according to claim 1, wherein said channel has a first volume and said fluid well has a second volume that is at least an order of magnitude greater than said first volume.

7. An apparatus, comprising:
   a body containing a fluid well designed and configured to receive a fluid having a first portion and a second portion;
   a structure exposed to an ambient environment capable of supporting partial evaporation of the fluid, said structure having:
   a longitudinal axis;
   a first end connected to said body;
   a second end spaced from said first end along said longitudinal axis; and
   a length from said first end to said second end;
   said structure containing a channel that extends along said length and defines a space that is in fluid communication with said fluid well and that receives a portion of the fluid from said fluid well, said channel:
   being dimensioned so as to wick the fluid from said fluid well via capillary action, into said space along said length from said first end substantially to said second end; and
   having an opening extending at least a substantial portion of the entirety of said length of said structure so that, when 1) said structure is exposed to the ambient environment, 2) said space in said channel is in fluid communication with the space is full of the fluid, and 3) the structure is exposed to the ambient environment, said opening allows the first portion of the fluid to evaporate from said space through said opening directly into the environment in a direction radial to said longitudinal axis along substantially the entirety of said length; and
   a material deposited in said space of said channel, wherein said material is composed essentially of the second portion of the fluid that was deposited via evaporation of the first portion of the fluid in said channel after the fluid was wicked into said channel via capillary action;
   wherein:
   said structure comprises a pair of spaced members extending along said length parallel to said longitudinal axis, said pair of spaced members together defining an open space that forms said channel and each having lateral sides spaced from one another and extending parallel to said longitudinal axis said open space being in fluid communication with the ambient environment along said lateral sides at a cross-section transverse to said longitudinal axis; and
   each of said pair of spaced members are cantilevered from said body.

8. The apparatus according to claim 7, wherein said pair of spaced members are connected by at least one support extending between said pair of spaced members within said channel.

9. The apparatus according to claim 7, wherein at least one of said pair of spaced members includes at least one opening exposing said channel to the ambient environment.

10. The apparatus according to claim 7, wherein at least one of said pair of spaced members comprises multiple layers.

11. The apparatus according to claim 7, wherein said structure includes a pair of electrodes located on opposing sides of said channel.

12. The apparatus according to claim 7, wherein said channel has a first volume and said fluid well has a second volume that is at least an order of magnitude greater than said first volume.

13. The apparatus according to claim 7, wherein said material comprises a mass-sensitive material selected as a function of an analyte so that the apparatus functions as a mass-sensitive sensor for the analyte.

14. The apparatus according to claim 13, wherein the analyte is a gas-borne biological or organic analyte and said material comprises a polymer that is mass-sensitive to the gas-borne biological or organic analyte.

15. The apparatus according to claim 13, further comprising a sensor for sensing a change in mass of said material as said mass increases by addition of the analyte to said material.

* * * * *